US007173020B2

(12) United States Patent
Borch et al.

(10) Patent No.: US 7,173,020 B2
(45) Date of Patent: Feb. 6, 2007

(54) PHOSPHORAMIDATES AND METHODS THEREFOR

(75) Inventors: Richard F. Borch, Lafayette, IN (US); Hugo Garrido-Hernandez, West Lafayette, IN (US); Sandra C. Tobias, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/053,024

(22) Filed: Feb. 8, 2005

(65) Prior Publication Data

US 2005/0171060 A1 Aug. 4, 2005

Related U.S. Application Data

(62) Division of application No. 09/822,376, filed on Mar. 30, 2001, now Pat. No. 6,903,081.

(60) Provisional application No. 60/193,918, filed on Mar. 31, 2000.

(51) Int. Cl.
*A61K 31/664* (2006.01)

(52) U.S. Cl. .............................. 514/137; 514/7; 514/43; 514/49; 514/75; 514/119

(58) Field of Classification Search ................ 514/137, 514/7, 43, 49, 75, 119
See application file for complete search history.

(56) References Cited

U.S. PATENT DOCUMENTS 5,233,031 A    8/1993  Borch et al.
5,472,956 A   12/1995  Borch et al.

FOREIGN PATENT DOCUMENTS

WO      WO 93 06120 A      4/1993

OTHER PUBLICATIONS

Chen et al., "The synthesis of O-monosaccharideyl-methoxycarbonyl-phosphonamidates by Arbuzov reaction", *Chinese Chemical Letters*, vol. 6, No. 1, 1995, pp. 23-26.
Siddiqui et al., "Design and synthesis of lipophilic phosphoramidate D4T-MP prodrugs expressing high potency against HIV in cell culture: Structural determinants for in vitro activity and qsar", *Journal of Medical Chemistry*, vol. 42, No. 20, 1999, pp. 4122-4128.
McGuigan et al., "Phosphoramidates as potent prodrugs of anti-HIV nucleotides: Studies in the amino region", *Antiviral Chemistry and Chemotherapy*, vol. 7, No. 1, 1996, pp. 31-36.
Meyers et al., "Design and synthesis of novel nucleotide prodrugs", American Association for Cancer Research, 2000, Abstract No. 100710.
Kolibaba et al., "Protein tryosine kinases and cancer", *Biochim. Biophys. Acta*, vol. 1333, 1997, pp. F217-F248.
Van der Geer et al., "Receptor protein-tyrosine kinases and their signal transduction pathways", *Ann. Rev. Cell. Bio.*, vol. 10, 1994, pp. 251-337.
Moran et al., "Src homology 2 domains direct protein-protein interactions in signal transduction", *PNAS, USA*, vol. 87, 1990, pp. 8622-8626.
Anderson et al., "Binding of SH2 domains of phospholipase C gamma 1, GAP and Src to activated growth factor receptors", *Science*, vol. 250, 1990, pp. 979-982.
Cantley et al., "Oncogenes and signal transduction", *Cell*, vol. 64, 1991, pp. 281-302.
Songyang et al., "Recognition and specificity in protein tryosine kinase-mediated signalling", *TIBS*, vol. 20, 1995, pp. 470-475.
Saltiel et al., "Targeting signal transduction in the discovery of antiproliferative drugs", *Chem. and Biol.*, vol. 3, 1996, pp. 887-893.
Gilmer et al., "Peptide inhibitors of Src SH3-SH2 phosphoprotein interactions", *J. Biol. Chem.*, vol. 269, 1994, pp. 31711-31719.
Lunney et al., "Structure-based design of a novel series of nonpeptide ligands that bind to the pp60$^{src}$ SH2—domain", *J. Am. Chem. Soc.*, vol. 119, 1997, pp. 12471-12476.
Plummer et al., "Design, synthesis and cocrystal structure of a nonpeptide Src SH2 domain ligand", *J. Med. Chem.*, vol. 40, 1997, pp. 3719-3725.
Domchek et al., "Inhibition of SH2 domain/phosphoprotein association by a nonhydrolyzable phosphonopeptide", *Biochemistry*, vol. 31, 1992, pp. 9865-9870.
Burke et al., "Nonhydrolyzable phosphotyrosyl mimetics for the preparation of phosphatase-resistant SH2 domain inhibitors", *Biochemistry*, vol. 33, 1994, pp. 6490-6494.
Ye et al., "L-O-(2-malonyl)tyrosine: A new phosphotyrosyl mimetic for the preparation of Src homology 2 domain inhibitory peptides", *J. Med. Chem.*, vol. 38, 1995, pp. 4270-4275.
Burke et al., "Conformationally constrained phosphotyrosyl mimetics designed as monomeric Src homology 2 domain inhibitors", *J. Med. Chem.*, vol. 38, 1995, pp. 1386-1396.
Burke et al., "4'-O-[2-(2-fluoromalonyl)]-L-tyrosine: A phosphotyrosyl mimic for the preparation of signal transduction inhibitory peptides", *J. Med. Chem*, vol. 39, 1996, pp. 1021-1027.
Llinas-Brunet et al., "Phosphotyrosine-containing dipeptides as high-affinity ligands for the p56 lck SH2 domain", *J. Med. Chem.*, vol. 42, 1999, pp. 722-729.
Lee et al., "Acquisition of high-affinity, SH2-targeted ligands via a spatially focused library", *J.Med. Chem*, vol. 42, 1999, pp. 784-787.
Beaulieu et al., "Ligands for the tyrosine kinase p56lck SH2 domain: Discovery of potent dipeptide derivatives with monocharged, nonhydrolyzable phosphate replacements", *J. Med. Chem.*, vol. 42, 1999, pp. 1757-1766.
Fries et al., Synthesis and biological evaluation of 5-fluoro-2'-deoxyuridine phosphoamidate analogs, *J. Med. Chem.*, vol. 38, 1995, pp. 2672-2680.
Meyers et al., "Synthesis and Biological Activity of Novel 5-Fluro-2'-deoxyuridine Phosphoramidate Prodrugs," Journal of Medicinal Chemistry, vol. 43, No. 22, 2000, pp. 4313-4318.
Borch et al., "Synthesis and Evaluation of Nitroheterocyclic Phorphoramidates as Hypoxia-Selective Alkylating Agents," Journal of Medicinal Chemistry, vol. 43, No. 11, 2000, pp. 2258-2265.

*Primary Examiner*—David Lukton
(74) *Attorney, Agent, or Firm*—Barnes & Thornburg LLP

(57) ABSTRACT

Novel phosphoramidate derivatives of hydroxy functional or amino functional compounds, including amino acids, peptides, peptidomimetics and nucleotide analogs, are described. The compounds enable enhanced intracellular delivery of drugs as their corresponding phosphate esters or amides. Described phosphoramidate compounds exhibit antiproliferative activity. Pharmaceutical formulations are provided for treatment of cancers.

17 Claims, No Drawings

PHOSPHORAMIDATES AND METHODS THEREFOR

CROSS REFERENCE TO RELATED APPLICATIONS

This application is a divisional of U.S. patent application Ser. No. 09/822,376, filed Mar. 30, 2001, now U.S. Pat. No. 6,903,081 which claims priority to U.S. Provisional Patent Application No. 60/193,918, filed Mar. 31, 2000, now abandoned, the disclosure of each of which is incorporated herein by reference.

GOVERNMENT RIGHTS

Research relating to this invention was supported in part by the U.S. Government under Grant No. RO1 CA34619 awarded from the National Cancer Institute. The U.S. Government may have certain rights in this invention.

FIELD OF THE INVENTION

This invention relates to intracellular delivery of phosphate-substituted therapeutic compounds. More particularly, the invention is directed to certain phosphate precursors and methods and intermediates therefor.

BACKGROUND AND SUMMARY OF THE INVENTION

Significant research efforts have been directed towards developing systems for enhancing the intracellular delivery of phosphate-substituted compounds, such as biologically active peptides and nucleotides, inasmuch as the high negative charge of these compounds leads to very low cellular permeability. For example, there is much interest in the intracellular delivery of tyrosine phosphate peptides and peptidomimetics for use in blocking the uncontrolled proliferation of tumor cells. In this regard, protein tyrosine kinases are important regulators of cell cycle progression, and represent attractive targets for the rational design of novel anticancer agents. Protein tyrosine kinases are activated upon phosphorylation of specific tyrosine residues of the kinases and the phosphotyrosine residue along with the three adjacent amino acids (pY-E-E-I) serve as a binding site for Src homology 2 (SH2) domains of intracellular signaling proteins. Interaction between an SH2 domain of an intracellular signaling molecule and an activated protein tyrosine kinase is essential for effective cell cycle progression. Thus, molecules that mimic the phosphotyrosine moiety of protein tyrosine kinases and block the binding of protein tyrosine kinases to SH2 domains represent promising antiproliferative agents for the treatment of cancers.

The phosphate dianion on tyrosine-phosphorylated protein tyrosine kinases is critical to the kinase-SH2 domain interaction. The crystal structures of a number of ligand-SH2 domains have been reported, the interactions have been modeled, and many different inhibitors have been synthesized. In all of these phosphotyrosine peptides and peptidomimetic inhibitors, the phosphotyrosine residue is involved in a complex network of hydrogen bonding and charge-charge interactions that require extensive interaction of the SH2 domain with the phosphate dianion of the tyrosine phosphate moiety. The importance of this dianionic interaction is illustrated by the fact that substitution of the phosphate group with a wide variety of other anionic and neutral hydrogen-bonding substituents leads to a significant loss in binding affinity. Thus, the intracellular delivery of tyrosine phosphate peptides and peptidomimetics where the phosphate is in the form of the dianion is critical.

Nucleotide analogs represent another class of promising agents for use in treating disease states caused by uncontrolled viral or cellular replication. Like tyrosine phosphate peptidomimetics, the phosphate dianion of nucleotide analogs is critical to the capacity of these compounds to block viral or cellular replication. The most widely used approach for the use of nucleotide analogs as therapeutic agents is to deliver the nucleoside analog as a prodrug across the cell membrane and to rely on the cellular machinery to link a phosphate group to the purine or pyrimidine base to form the corresponding nucleotide analog. However, many nucleosides with therapeutic promise are not converted to the corresponding nucleotide by existing cellular pathways. Furthermore, tumor cells or virus-infected cells may become resistant to treatment by down-regulating the activity of nucleoside kinases, and, for many previously developed nucleotide prodrugs, the intracellular activation process is so inefficient that effective nucleotide concentrations do not accumulate within the cell.

The general strategy for the intracellular delivery of phosphate-containing compounds utilized in the present invention is outlined in Scheme 1:

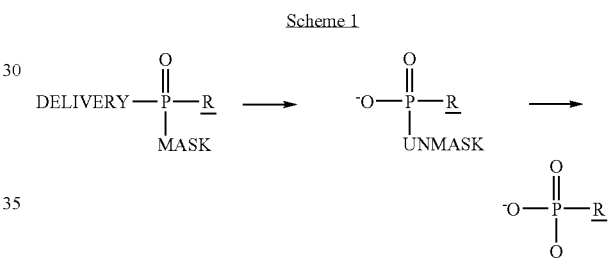

Briefly, the phosphate-substituted compound to be delivered intracellularly is synthesized (R with attached phosphate in scheme 1 above) and is linked to a delivery group and a masking group. The masking group consists of a haloalkylamine moiety that is hydrolyzed intracellularly to produce an intermediate that is stable as long as the delivery group remains intact, but is released upon intracellular activation of the delivery group. The delivery group may be a group, such as a nitrofuryl group or a perhydrooxazine, that is subject to intracellular hydrolysis to provide an intermediate which undergoes cyclization and P—N bond cleavage (i.e., spontaneous hydrolysis) in the intracellular environment releasing the desired phosphate-containing compound.

Systems for the intracellular delivery of alkylating agents and nucleotides that employ chemistry related to that described in scheme 1 have been developed previously. However, previous methods resulted in only about 50% intracellular conversion to the desired nucleotide with the other 50% of the prodrug being "lost" as a biologically inactive solvolysis product. The present invention is directed to a newly discovered modification of this chemistry that extends its applicability both to nucleotide analogs and to the phenol phosphate group that is the essential constituent of tyrosine phosphate peptides and peptidomimetics. The invention is based on the discovery that changing the structure of the masking group from a haloethyl to a halobutyl (or halopentyl) group results in the rapid and quantitative intracellular conversion (i.e., about 100% conversion) to the desired nucleotide or phosphate-containing peptide. The new chemistry of the invention is applicable to nucleotide analogs, phosphotyrosine peptides and peptidomimetics, and to a wide variety of other pharmaceutically significant compounds containing phosphate moieties.

The development of protected phosphotyrosine precursor phosphoramidates in accordance with this invention enables facile synthesis of phosphotyrosine peptides and peptidomimetics. Thus, the invention is also directed to protected phosphotyrosine precursors and related protected peptides, for example, with N-BOC and fluorenylmethoxycarbonyl groups.

In one embodiment of this invention there is provided a phosphoramidate prodrug compound wherein a biologically active compound having hydroxy functionality is covalently linked through that hydroxy functionality to form a biologically labile phosphoramidate which is converted intracellularly to the corresponding drug phosphate. The biologically labile phosphoramidate group enables more efficient intracellular delivery of the drug substance and serves as a means for achieving biologically significant intracellular concentrations of the drug substance in the form of its corresponding phosphate ester. In another embodiment the biologically active compound has amino functionality, and it is linked through that amino functionality to form a biologically labile phosphoramidate which is converted intracellularly to the phosphoramide ($^-OPO_2NH$-Drug).

In another embodiment this invention provides an intermediate halophosphoramidite of the formula

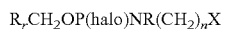

wherein n is 4 or 5, R is lower alkyl or $—(CH_2)_nX$, X is an electrophilic group capable of being nucleophilically displaced from the carbon atom to which it is bound and the group $R_rCH_2—$ is a biologically labile ester forming group, more particularly, an ester forming group that is readily hydrolyzed intracellularly. This compound can be used as an intermediate reagent for preparing the above-described phosphoramidate prodrug compounds using a method embodiment of this invention wherein the biologically active compound (Drug-OH) is reacted with that halophosphoramidite intermediate to form the corresponding drug reacted intermediate

which is then oxidized to form the phosphoramidate prodrug. The method can be used to form phosphoramidite precursors of intracellular drug phosphates starting with hydroxy functional amino acids having carboxyl and amino functional groups protected with standard protecting groups or from biologically active peptides or peptidomimetics or nucleotide analogs. The phosphoramidate prodrugs in accordance with this invention are converted to the corresponding phosphates following hydrolysis of the $R_rCH_2—$ ester forming group. Subsequent hydrolysis of the cyclized 5- or 6-membered zwiterionic intermediate (formed by cyclization of the group $—N(CH_2)_nX$) provides the corresponding phosphate as the exclusive phosphorous-containing product. Analogous synthetic procedures can be carried out with active compounds having amino functionality represented generally herein as Drug $NH_2$.

DETAILED DESCRIPTION OF THE INVENTION

The present invention is directed to novel prodrug chemistry designed to deliver peptide and peptidomimetic phosphates and nucleotide or nucleotide analog phosphates into cells across cell membranes. In one embodiment of the present invention there is provided an intermediate compound of the formula

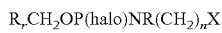

wherein

R is $C_1-C_4$ alkyl or $—(CH_2)_nX$;

n is 4 or 5;

X is an electrophilic group capable of being nucleophilically displaced from its bonded carbon atom;

halo is chloro, bromo or iodo; and the group $R_rCH_2—$ is a biologically labile ester forming group.

The electrophilic group X is preferably halo, for example, chloro, bromo, or iodo. However, the nature of that group is not critical provided that it can serve as a good leaving group to enable cyclization and concomitant quaternization of the phosphorous-bound nitrogen atom in vivo following administration of the phosphoramidite prodrugs in accordance with this invention. Other electrophilic leaving groups such as acetate, methane sulphonate, trifloromethane sulfonate, haloacetate and the like can be used.

The term "biologically labile ester forming group" as used in defining this invention refers to those ester forming groups derived from alcohols that form ester derivatives that are stable under drug manufacture and storage conditions but are subject to hydrolysis when exposed to biological conditions in vivo. Preferably, the ester forming groups used in accordance with the present invention exhibit minimal susceptibility to hydrolysis in the body fluids in the extracellular space but exhibit susceptibility to hydrolysis in the intracellular space where ester-degrading reductive conditions are prominent. Thus, in one embodiment of the present invention the biologically labile ester forming group on the phosphoramidate prodrugs of this invention are those ester forming groups that are susceptible to hydrolysis under mild reductive conditions which include those groups wherein $R_r$ is nitroaryl including nitrofuryl, nitrothienyl, nitropyrroyl, nitroimidazoyl, and the like, indanyl, napthoquinolyl and perhydrooxazine. The nature of the ester forming group $R_rCH_2—$ is not critical provided that the group exhibits susceptibility to hydrolysis under intracellular conditions, typically biological conditions that exhibit reductive potential.

The therapeutic compounds that can be derivatized in accordance with this invention to form the present phosphoramidate prodrug compounds include amino acids, necessarily in the form of their doubly protected (both carboxyl protected and amino protected) form, peptides, proteins, peptidomimetics, nucleotide analogs, and other hydroxy functional drug compounds that can exhibit biological activity as their corresponding phosphates. In one preferred embodiment of this invention, the drug is derivatized to the corresponding phosphoramidate in accordance with this invention is a nucleotide analog, such as fluorodeoxyuridine, which exhibits anti-tumor activity as its corresponding monophosphate derivative. In another embodiment the drug is an amino acid, a peptide or a peptidomimetic.

The phosphoramidate prodrug compounds in accordance with this invention can be prepared from the corresponding hydroxy functional drug substances by any one of several synthetic routes. In one preferred embodiment, the phosphoramidate prodrug is prepared by a method comprising the steps of reacting the hydroxy functional drug compound with a compound of a formula $$R_rCH_2OP(halo)NR(CH_2)_nX$$

under conditions conducive to the formation of an intermediate compound of the formula $$R_rCH_2OP(O\text{-Drug})NR(CH_2)_nX$$

and thereafter oxidizing that intermediate to form the present phosphoramidate prodrug of the formula $$R_rCH_2OP(O)(O\text{-Drug})NR(CH_2)_nX$$

in which formulas $R_r$, R, n, and X are as defined above. The conditions for forming the intermediate compound of the formula $$R_rCH_2OP(O\text{-Drug})NR(CH_2)_nX$$

can be varied widely, however, it is preferred that the reaction be carried out at low temperature in the presence of an acid scavenger, such as a tertiary amine base. In one embodiment the reaction is carried out at low temperature (about −70° C. to about −10° C. using dry pyridine as the reaction medium. The oxidation of the intermediate compound of the formula $$R_rCH_2OP(O\text{-Drug})NR(CH_2)_nX$$

to the present phosphoramidate prodrug compound of the formula $$R_rCH_2OP(O)(O\text{-Drug})NR(CH_2)_nX$$

can be carried out as well under a wide variety of mild oxidizing conditions. The nature of the oxidant is not critical provided that it is capable of affecting the required oxidation of the phosphorous atom to the +5 oxidation state. Examples of oxidizing agents include peracids, peroxides, hydroperoxides and the like. The oxidation is typically carried out at temperatures less than about 0° C., although such is not critical.

The intermediate halo phosphoramidite of the formula $$R_rCH_2OP(O\text{-Drug})NR(CH_2)_nX$$

is typically prepared by reacting phosphorous trichloride at low temperature with an alcohol of the formula $R_rCH_2OH$ in an inert organic solvent in the presence of a tertiary amine base, and the resulting product is reacted with an amine of the formula $HNR(CH_2)_nX$. Preferably that intermediate is generated immediately prior to its reaction with the hydroxy functional drug compound, typically in the presence of an acid scavenger, to form the present phosphoramidate prodrug.

In one alternate method of preparing the phosphoramidate prodrugs of this invention the hydroxy functional drug compound is reacted with a chlorophosoramidate intermediate derived from a reaction sequence starting with phosphorous oxytrichloride (as opposed to phosphorous trichloride) using the same general reactants and conditions described above except that the last oxidation step is eliminated.

Each of the foregoing reactions can be carried out in a similar manner using an amino functional drug (Drug $NH_2$) to provide the corresponding compounds $$R_rCH_2OP(O)(NH\text{ Drug})NR(CH_2)_nX$$

In another embodiment of the invention a method is provided of preparing a compound of the formula $$R_rCH_2OP(O)_m(halo)NR(CH_2)_nX$$

comprising the steps of reacting a compound of the formula $$P(O)_mhalo_3$$

with 1) an alcohol of the formula $R_rCH_2OH$ and 2) an amine of the formula $HNR(CH_2)_nX$, each in the presence of an acid scavenger, wherein in the above formulas
  m is 0 or 1;
  R is $C_1$–$C_4$ alkyl or —$(CH_2)_nX$;
  n is 4 or 5;
  X is an electrophilic group capable of being nucleophilically displaced from its bonded carbon atom;
  halo is chloro, bromo or iodo; and
  the group $R_rCH_2$— is a biologically labile ester forming group.

In yet another embodiment of the invention a method is provided of preparing a phosphoramidate prodrug of the formula $$R_rCH_2OP(O)(O\text{-Drug})NR(CH_2)_nX$$

for enhanced intracellular drug delivery of a compound of the general formula Drug-OPO$_3$. The method comprises the steps of reacting a therapeutic compound of the formula Drug-OH with a compound of the formula $$R_rCH_2OP(O)(halo)NR(CH_2)_nX$$

under conditions conducive to the formation of the prodrug wherein in the above formulas
  R is $C_1$–$C_4$ alkyl or —$(CH_2)_nX$;
  n is 4 or 5;
  X is an electrophilic group capable of being nucleophilically displaced from its bonded carbon atom;
  halo is chloro, bromo or iodo; and
  the group $R_rCH_2$— is a biologically labile ester forming group.

As noted above the chemistry described herein can be applied using the same or similar reaction conditions to the preparation of prodrug phosphoramidates of the formula $$R_rCHOP(O)(NH\text{-Drug})NR(CH_2)_nX$$

by reaction of the intermediate compound $$R_rCHOP(O)(halo)NR(CH_2)_nX$$

with a biologically active compound of the general formula Drug-NH$_2$ wherein $R_r$, halo, R, n and X are as defined hereinabove. This chemistry provides a means for intracellular delivery of therapeutic compounds of the formula Drug-NHPO$_3$. Thus, for example, 5'-amino nucleotides or nucleotide analogs can be derivatized as the corresponding prodrug phosphoramidates for efficient intracellular delivery of the corresponding 5'-NHPO$_3$ derivatives.

The phosphoramidite compounds of the present invention are either themselves prodrugs or, for example, in the instance of tyrosine phosphoramidates, they can be used in the synthesis of peptide or peptidomimetic prod rugs. It will be recognized by those of ordinary skill in the art that the chemistry involved in the synthesis of the phosphoramidites of the present invention is such that the hydroxy, carboxy, thiol, and amine functional groups on the starting drug compound that are not intended to be involved in the chemistry of the phosphoramidate synthesis, should be protected with an art-recognized protecting group. The literature is replete with reference to such protecting groups, their application to protect various functional groups and the conditions for their removal. The use of such protecting groups is well known to those ordinary skill in the art and their use in implementing the synthesis of the present phosphoramidite prodrugs and intermediates therefor form no part of the present invention.

The phosphoramidite prodrugs prepared in accordance with the present invention can be formulated and used in the same or similar dosage forms as the underivatized drug compounds using art-recognized techniques.

In one embodiment of the invention a reaction as outlined in scheme 2 is performed:

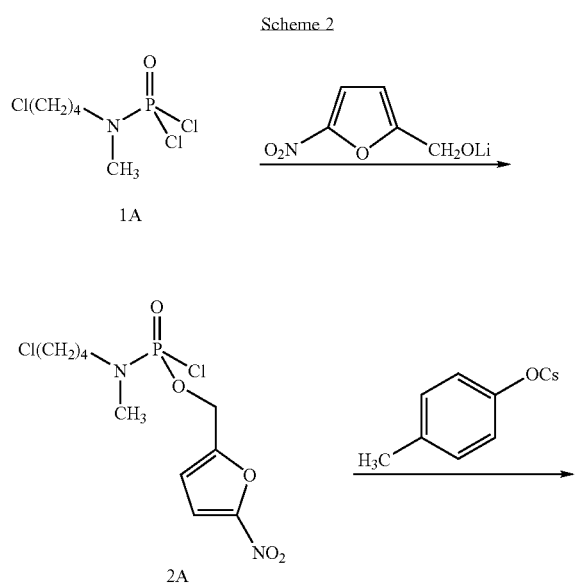

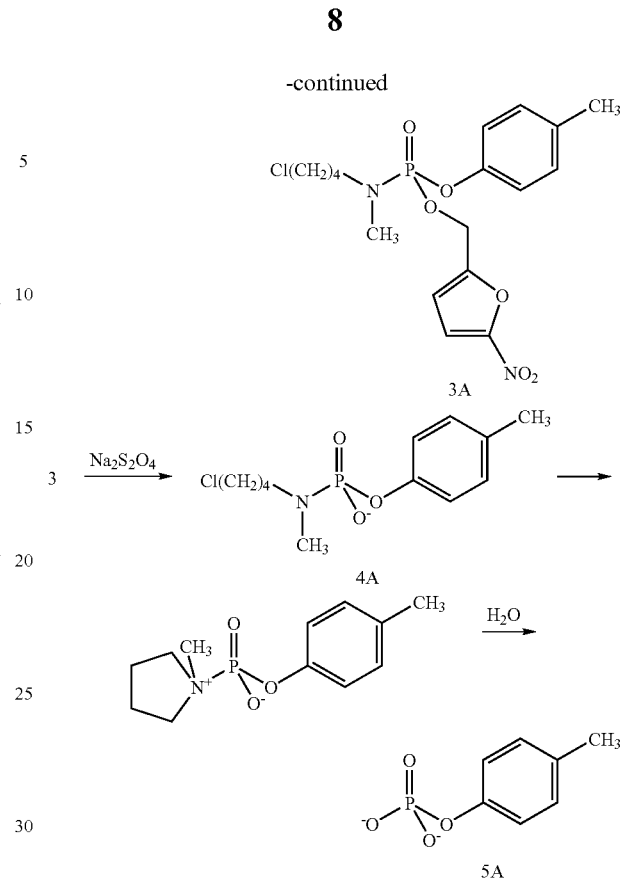

In this reaction, prodrug 3A was synthesized by sequential addition of nitrofuryl alcohol and p-cresol to phosphoramidic dichloride 1. Prodrug 3 was then activated by reduction with sodium dithionite in ethanol/aqueous buffer, which reduces the nitrofuryl group and leads to the expulsion of phosphoramidate anion 4A. Subsequent reaction of this intermediate was monitored by $^{31}$P nmr. Intermediate 4A underwent smooth cyclization to the 5-membered zwitterionic intermediate, and attack by water gave the cresol phosphate as the exclusive phosphorus-containing product by nmr.

An alternate embodiment of the invention is illustrated in scheme 3:

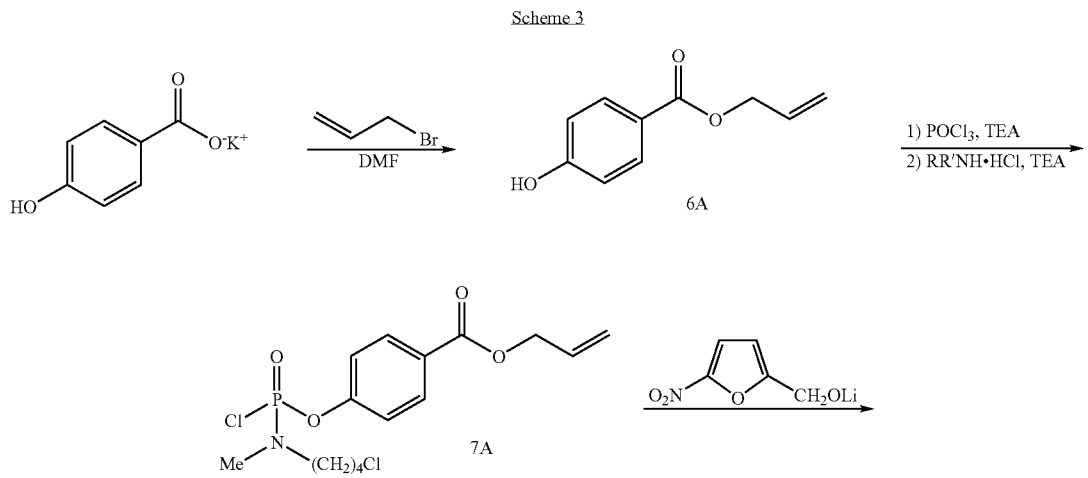

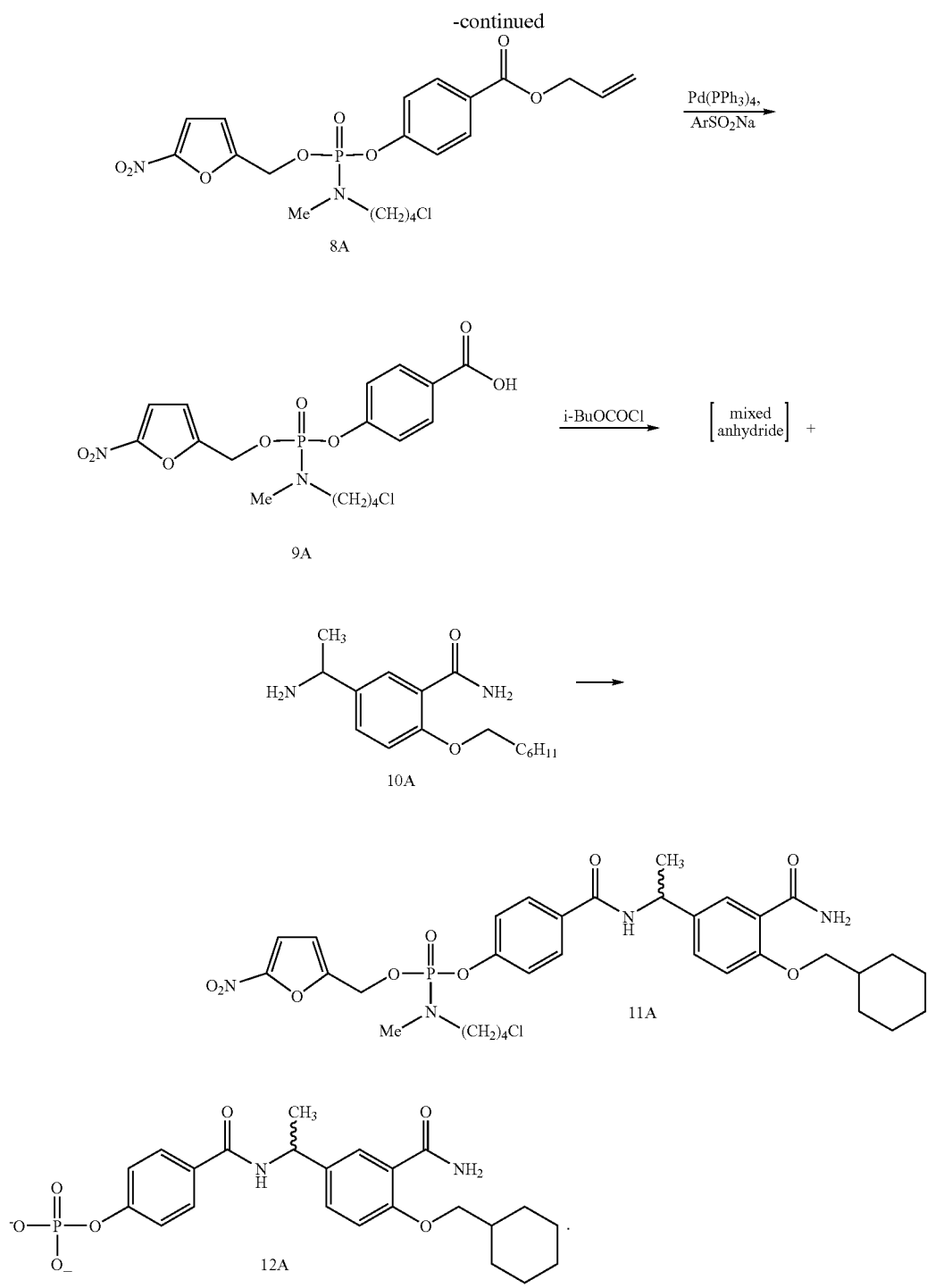

This reaction is directed toward the synthesis of phosphoramidate 11A and involved the preparation of the nitrofuryl phosphoramidate of p-hydroxybenzoic acid 9A and coupling of this product with the benzyl amine 10A, prepared from 5-acetylsalicylamide. Briefly, to synthesize the benzoic acid derivative 9A, p-Hydroxybenzoic acid was converted to its allyl ester 6A by reaction of the potassium salt with allyl-bromide. The allyl ester was reacted with POCl₃ and the intermediate phosphoryl dichloride was treated with methyl chlorobutylamine in the presence of triethylamine to give phosphoramidic chloride 7A. Reaction of 7A with the lithium salt of 5-nitro-2-hydroxymethylfuran afforded the phosphoramidate 8A. Deprotection of the allyl ester was accomplished by reaction with Pd(Ph₃P)₄/sodium p-toluenesulfinate to give the benzoic acid phosphoramidate 9A. Reaction of 9A with isobutyl chloroformate in the presence of triethylamine, followed by addition of benzylamine 10A afforded the desired peptidomimetic prodrug 11A. In order to confirm that the activation chemistry of 11A to 12A would proceed as expected, 11A was reduced with sodium dithionite in ethanol/aqueous buffer and the reaction monitored by $^{31}$P nmr. Conversion of 11 to the phosphoramidate anion was complete within minutes; the phosphoramidate anion was smoothly and exclusively converted to the phosphate 12A with a half-time of 21 minutes at 37° C. The phosphate 12A corresponding to activation of 11A has been synthesized and shown to bind to the pp60$^{src}$ SH2 domain with a binding affinity of 5.6 μM.

In yet another embodiment of the invention, a different intermediate was used for incorporation into the series of reactions depicted in Scheme 3 to form a tyrosine phosphate phosphoramidate. The intermediate 17A is shown below along with the products that result when the reactions depicted in Scheme 3 are performed (see Scheme 3a):

Scheme 3a

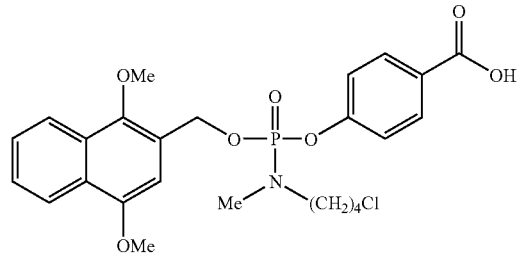

17A

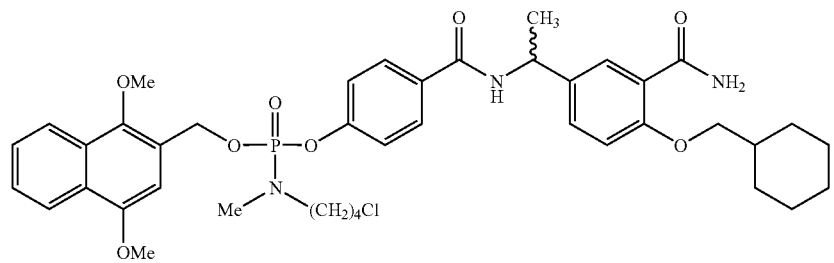

18A

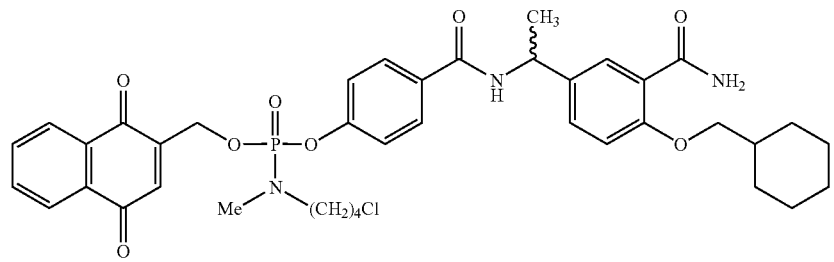

19A

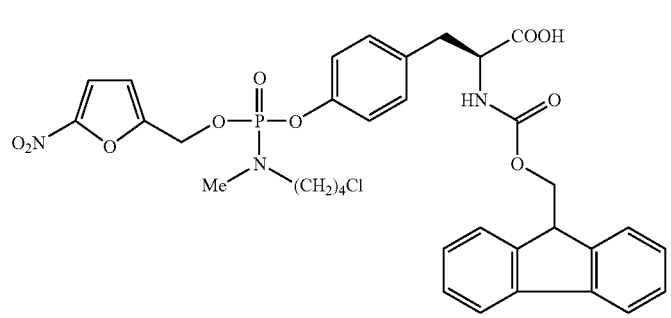

20A

The intermediate 17A was prepared as described for compound 9A in Scheme 3, except that 2-hydroxymethyl-1,4-dimethoxynaphthalene was used instead of 5-nitro-2-hydroxymethylfuran in the third step of the reaction series. Compound 17A was then coupled with amine 10A (Scheme 3) to give the amide 18A using new conditions that generate a high yield of purified product in minutes. Finally, the dimethoxynaphthalene 18A is converted smoothly to the naphthoquinone 19A by oxidation with ceric ammonium nitrate.

In still another embodiment of the invention, masked phosphotyrosine-containing peptides are synthesized as depicted in scheme 4:

Removal of the allyl protecting group gave the BOC-protected tyrosine phosphoramidate 16A in excellent overall yield. This analog should be suitable for coupling to a variety of amines and will also be valuable as a reagent in automated peptide synthesis.

The synthesis reaction depicted in scheme 4 has been extended to the development of protected tyrosine phosphoramidates containing the fluorenylmethoxycarbonyl (FMOC) protecting group. FMOC-protected amino acids are widely used in peptide synthesis and offer the advantage that the protecting group can be removed rapidly and cleanly under base-catalyzed conditions. The FMOC analog of tyrosine phosphoramidate 16A, compound 20A above (see

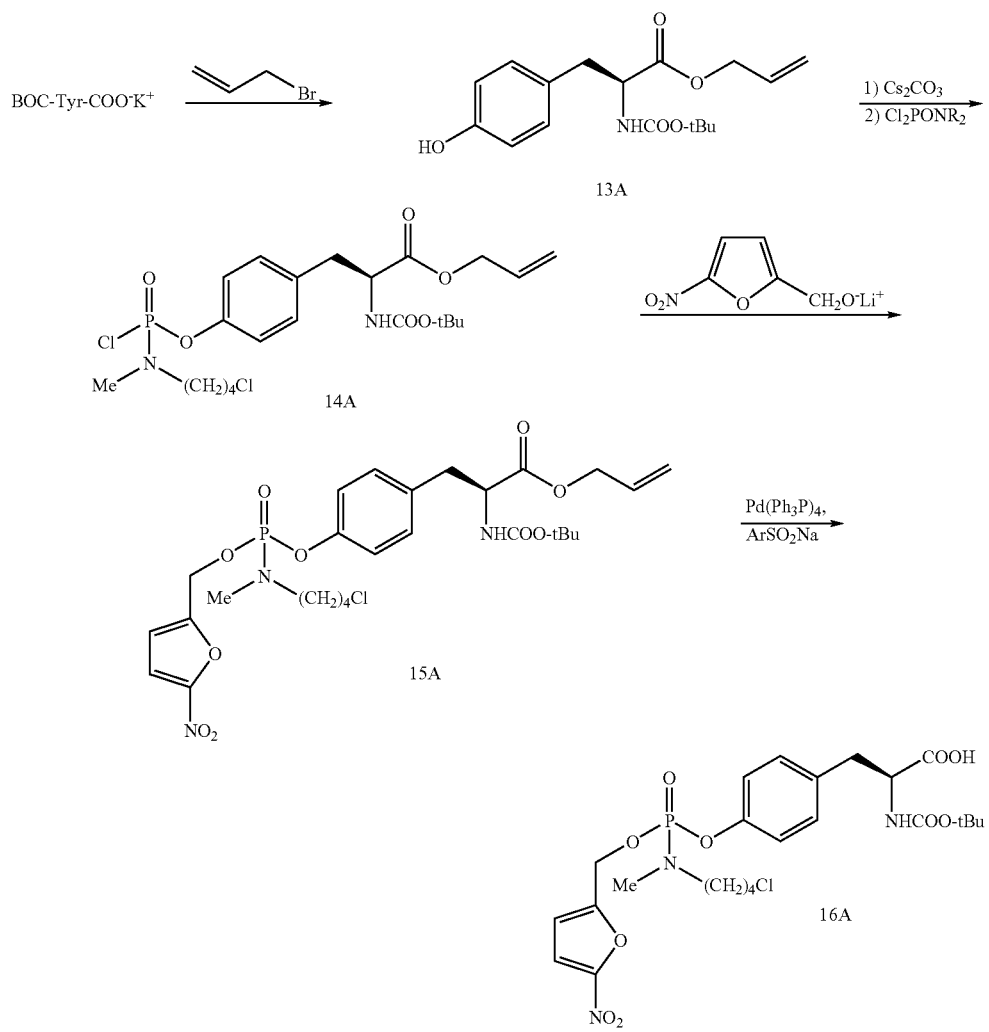

N-BOC-tyrosine potassium salt was reacted with allyl bromide to give BOC-tyrosine allyl ester 13A. The ester was converted to its cesium phenoxide salt and reacted with N-methyl-N-chlorobutyl phosphoramidic dichloride to give the adduct 14A. Finally, the phosphoramidic chloride was reacted with the lithium salt of 5-nitro-2-hydroxymethylfuran to give the tyrosine phosphoramidate ester 15A.

Scheme 3a) was prepared by a series of reactions similar to those outlined in Scheme 4. The FMOC protecting group is rapidly and cleanly removed by reaction with diazabicycloundecane in dichloromethane for 5 minutes. Finally, coupling reactions of 16A and 20A with methyl glycinate were carried out to demonstrate that these compounds can be used in peptide synthesis reactions.

In another embodiment of the present invention, synthesis of the nitrofuryl chlorobutyl nucleoside 3 was carried out in one operation without isolation of intermediates as shown in scheme 5:

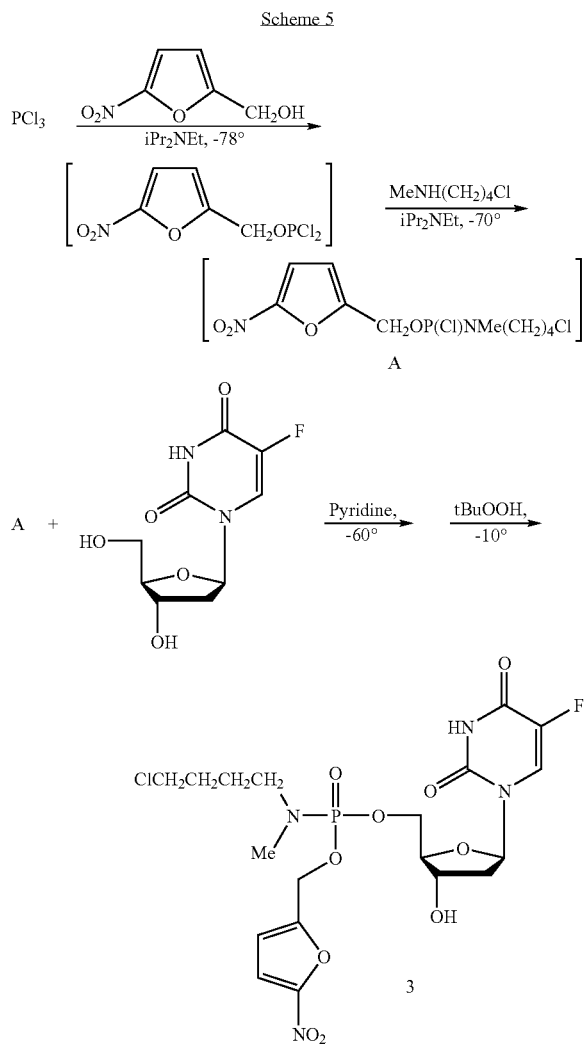

vitro. Cells were exposed to drug for 2, 8, 24, and 48 hours; the results are summarized below:

| Compound | L1210 IC$_{50}$ nM | | | |
|---|---|---|---|---|
| | 2 hr | 8 hr | 24 hr | 48 hr |
| 3 | 112 | 40 | 6.0 | 2 |
| 5-FU | 2742 | 1390 | 495 | 265 |

The chlorobutyl phosphoramidate 3 is significantly more potent than the analogous bromoethyl compound and is one of the most potent nucleotide prodrugs that we have prepared.

In a related embodiment of the invention, intermediate 4 was incorporated into the above-described reaction scheme and the new drug 5 was produced:

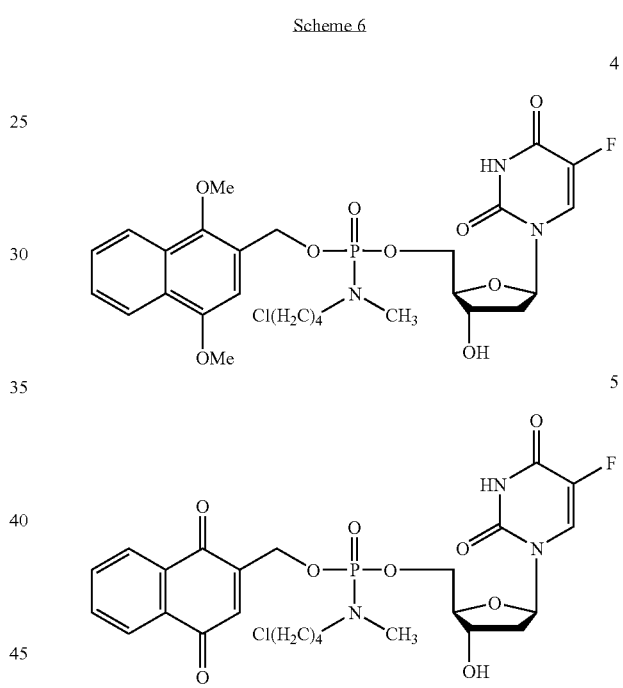

Phosphorus trichloride in methylene chloride was reacted with one equivalent of the nitrofuryl alcohol at −78° C. and the intermediate dichloride treated with the hydrochloride salt of N-methyl-N-chlorobutylamine to generate the monochloride intermediate A. A solution of 5-fluoro-2′-deoxyuridine in pyridine was added to this intermediate. The resulting phosphoramidate was oxidized with t-butyl hydroperoxide to give the nucleoside phosphoramidate 3. Yields in this synthesis are low and variable (20–60%).

In an alternate embodiment of the invention, the analogous thymidine compounds were prepared (i.e., 3 where F=CH$_3$). The thymidine phosphoramidate was activated by reduction of the nitrofuryl group with sodium dithionite in aqueous buffer/acetonitrile at 37° C., and the reaction was monitored by $^{31}$P nmr. Within ten minutes the resonance for the phosphoramidate anion had disappeared and a new peak corresponding to thymidine-5′-phosphate appeared as the exclusive phosphorus-containing product by $^{31}$P nmr. Nucleoside phosphoramidate 3 was then evaluated for its ability to inhibit proliferation of L1210 leukemia cells in The dimethoxynaphthalene analog 4 is synthesized in a manner analogous to that outlined in scheme 5, except that 2-hydroxymethyl-1,4-dimethoxynaphthalene is used instead of 5-nitro-2-hydroxymethylfuran in the first step. The dimethoxynaphthalene 4 is converted smoothly to the naphthoquinone 5 by oxidation with ceric ammonium nitrate. Compound 5 was evaluated an inhibitor of L1210 leukemia cell proliferation in comparison to compound 3 above:

L1210 IC$_{50}$, nM

| Cpd | 2 hr | 8 hr | 24 hr | 48 hr |
|---|---|---|---|---|
| 3 | 116 | 47 | 7.2 | 2.3 |
| 5 | 44 | 16 | 3.1 | 0.63 |
| 5-FU | 2500 | 1010 | 360 | 200 |

It is apparent that both compounds are highly potent inhibitors of L1210 cell proliferation, and compound 5 is approximately 3-fold more potent than compound 3 in this assay.

In one aspect of the invention the phosphoramidate prodrug is a compound of the formula

R$_f$CH$_2$OP(O)(Z-Drug)NR(CH$_2$)$_n$X formed using a hydroxy or amino functional peptidomimetic (Drug ZH) of the formula:

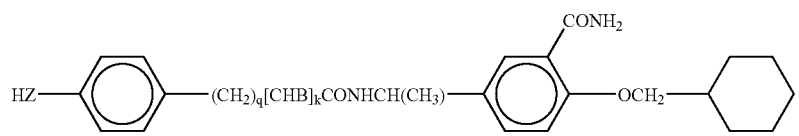

HZ—⟨⟩—(CH$_2$)$_q$[CHB]$_k$CONHCH(CH$_3$)—⟨⟩—OCH$_2$—⟨⟩ with CONH$_2$ substituent wherein Z is O or N;
q and k are independently 1 or 0, and
B is H, amino, protected amino, or C$_1$–C$_4$ alkanoylamino.

One group of such compounds are benzamido compounds wherein q and k are each 0, for example:

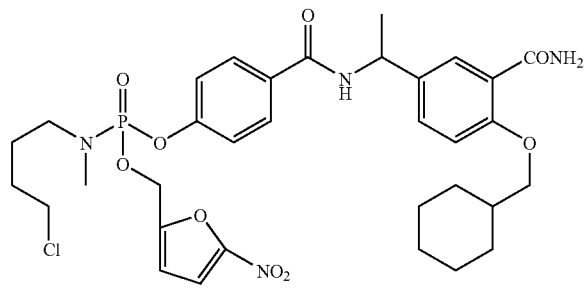

37

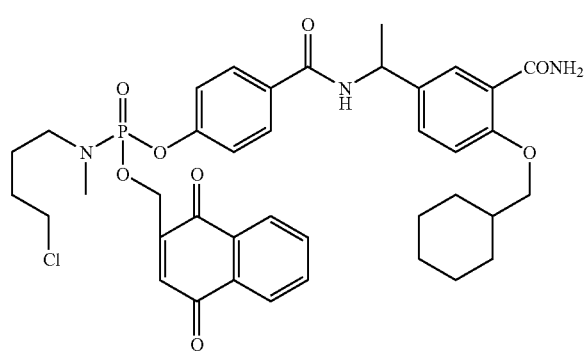

42

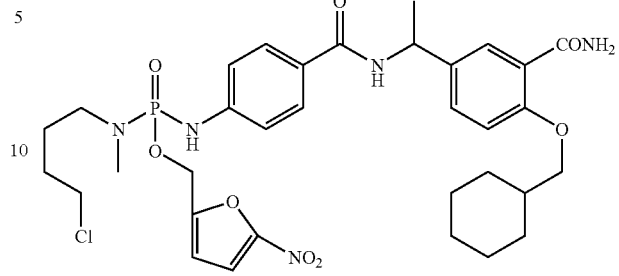

Another group of such compounds are phenylacetyl compounds wherein q is 1 and k is 0, for example:

40

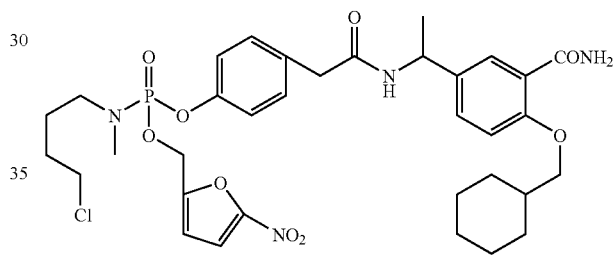

41

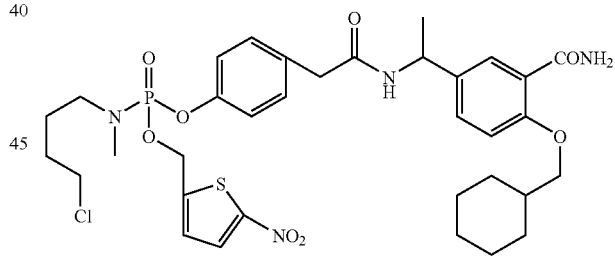

Still another group of peptidomimetics (Drug ZH) are tyrosyl derivatives wherein q is 1 and k is 1, for example:

38

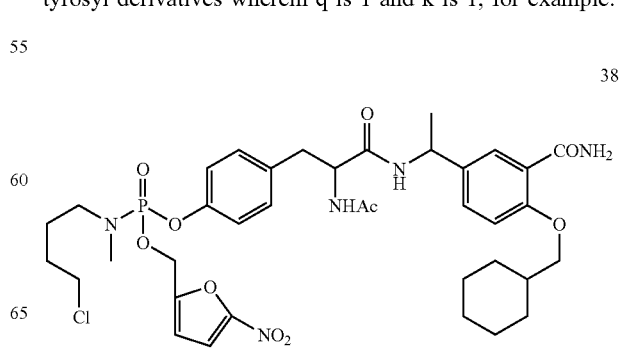

-continued

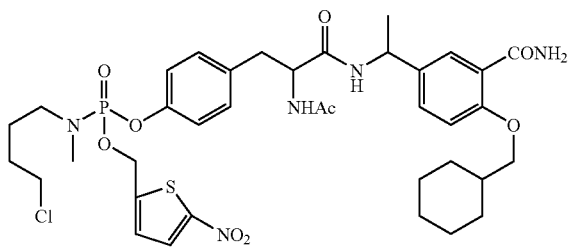
39

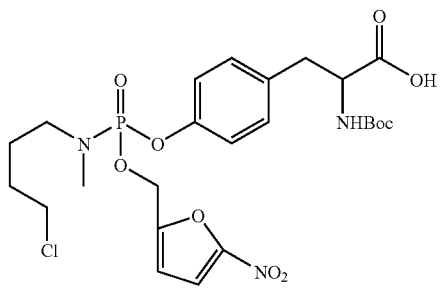
28

Several of such compounds have been found to exhibit significant inhibition of luciferase expression in transfected J77 cells, predictive of antiproliferative activity.

Several phosphoramidate compounds prepared in accordance with this invention wherein "Drug ZH" is a nucleotide analog have been found to exhibit significant growth inhibition in L1210 mouse leukemia cells. Such compounds are part of one preferred group of antiproliferative agents of this invention. Numerous nucleotide analogs have been reported in the literature to exhibit antiproliferative activity and any of such compounds, including those that can be covalently bound in the present phosphoramidates through a hydroxy or an amino functional group can be used in the preparation of the present compounds.

In still another embodiment of the invention the phosphoramidate compounds are derivatives of amino acids and amino acid esters of the formula

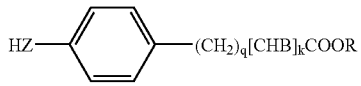

wherein Z, q, k and B are as defined above and R is hydrogen or a carboxy protecting group, particularly an ester forming group. Such tyrosine or tyrosine analogs are useful for the preparation of peptides or peptidomimetic compounds capable of facile transmembrane delivery as an intracellular corresponding source of the peptide phosphate or peptidomimetic phosphate. Alternatively such compounds can themselves provide an intracellular source of the corresponding amino acid or amino

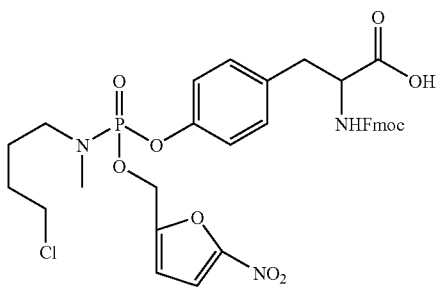
27 acid analog. Examples of such compounds are:

The present invention further provides pharmaceutical formulations comprising an effective amount of prodrug phosphoramidate compounds for treatment of cancers. As used herein, an effective amount of the prodrug compound is defined as the amount of the compound which, upon administration to a patient, inhibits growth/proliferation of tumor cells, kills malignant cells, reduces the volume or size of the tumors or eliminates tumors in the treated patient.

The effective amount to be administered to a patient is typically based on body surface area, patient weight, and patient condition. The interrelationship of dosages for animals and humans (based on milligrams per meter squared of body surface) is described by Freireich, E. J., et al., *Cancer Chemother. Rep.*, 50 (4): 219 (1966). Body surface area may be approximately determined from patient height and weight (see e.g., Scientific Tables, Geigy Pharmaceuticals, Ardley, N.Y., pages 537–538 (1970)). An effective amount of the phosphoramidate compounds of the present invention, can range from about 0.05 mg/kg to about 100 mg/kg, about 0.25 mg/kg to about 50 mg/kg, and most typically about 0.1 to about 10 mg/kg per dose. Effective doses will also vary, as recognized by those skilled in the art, dependent on route of administration, excipient usage and the possibility of co-usage with other therapeutic treatments, including other chemotherapeutic agents, and radiation therapy.

The pharmaceutical formulation may be administered via the parenteral route, including subcutaneously, intraperitoneally, intramuscularly and intravenously. Examples of parenteral dosage forms include aqueous solutions or suspensions of the active agent in isotonic saline, 5% glucose or other well-known pharmaceutically acceptable liquid carrier. In one aspect of the present pharmaceutical composition, the phosphoramidate compound is dissolved in a saline solution containing 5% of dimethyl sulfoxide and about 10% Cremphor EL (Sigma Chemical Company). Additional solubilizing agents such as cyclodextrins, which can form more soluble complexes with the present compounds, or other solubilizing agents well-known to those familiar with the art, can be utilized as pharmaceutical excipients for delivery of the present compounds for cancer therapy.

Alternatively, the present compounds can be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active phosphoramidate and solid carriers and lubricants well-known to those familiar with the art. Examples of solid carriers include starch, sugar, bentonite. The compounds of the present invention can also be administered in a form of a hard shell tablet or capsule containing, for example, lactose or mannitol as a binder and conventional fillers and tableting agents.

EXPERIMENTAL PROCEDURES AND EXAMPLES

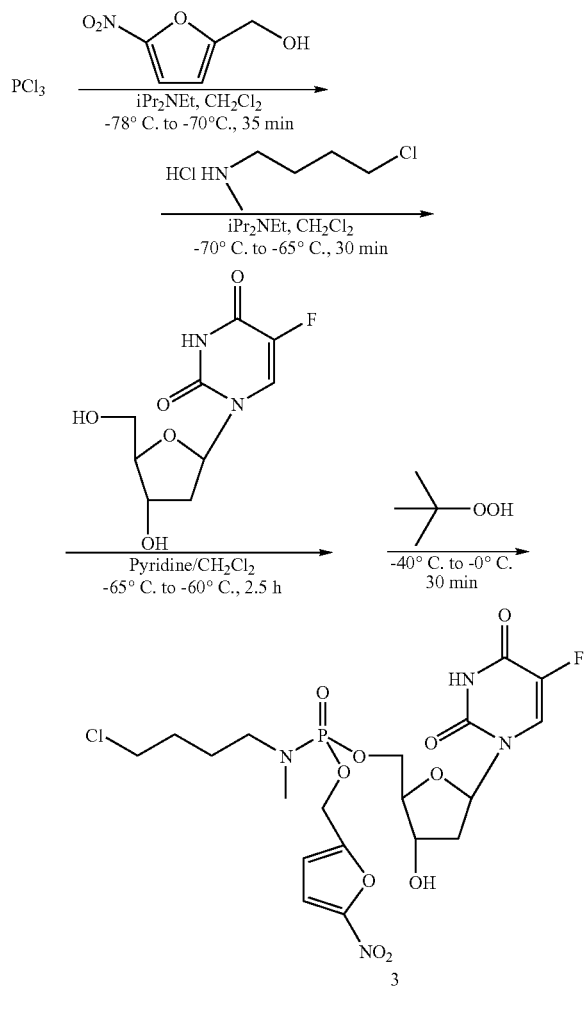

5-Fluoro-2'-deoxyuridyl 5-nitrofurfuryl N-methyl-N-(4-chlorobutyl)phosphoramidate (3)

Phosphorus trichloride (2M in CH$_2$Cl$_2$; 0.81 mL; 1.63 mmol) was cooled to −78° C. under argon. 5-Nitrofurfuryl alcohol (233 mg; 1.63 mmol) was dissolved in 12 mL of anhydrous CH$_2$Cl$_2$, added to cooled PCl$_3$ followed by dropwise addition of neat and anhydrous iPr$_2$NEt (0.57 mL; 3.25 mmol). The reaction was stirred between −78° C. and −70° C. for 15 min. N-Methyl-N-(4-chlorobutyl)amine hydrochloride (257 mg; 1.63 mmol) was dissolved in 16 mL of anhydrous CH$_2$Cl$_2$ added to the reaction mixture followed by dropwise addition of anhydrous and neat iPr$_2$NEt (1.13 mL; 6.50 mmol), and the reaction mixture was stirred between −78° C. and −70° C. for 30 min. The reaction mixture was cannulated to a solution of 5-fluoro-2'-deox- yuridine (200 mg; 0.812 mmol) in 2 mL of anhydrous CH$_2$Cl$_2$ and 2 mL of anhydrous pyridine precooled to −65° C. The reaction was stirred between −65° C. and −60° C. for 1 hour. t-Butylhydroperoxide (4.6M in decane; 0.44 mL) was added to the reaction mixture that was stirring at −65° C. The temperature was increased to −40° C. and stirred from −40° C. to 0° C. over 30 min. The reaction mixture was ran through a plug of celite and concentrated under reduced pressure. Column chromatography of the crude product (1:1 CH$_2$Cl$_2$/acetone) afforded 1 (155 mg; 34%) as a yellow foam.

$^1$H NMR (CDCl$_3$): d 9.68 (m, 1H); 7.80 and 7.74 (d, 1H, J=6.22 Hz and 6.41 Hz); 7.30 (d; 1H, J=3.48 Hz); 6.71 (d, 1H, J=3.30); 6.22 (m, 1H); 5.03 (m, 2H); 4.52 (m, 1H); 4.24 (m, 2H); 4.07 (m, 1H); 3.57 (m, 2H); 3.07 (m, 2H); 2.68 (d, 3H, J=10.25 Hz); 2.49 (m, 1H); 2.18 (m, 1H), 1.74 (m, 4H). $^{31}$P NMR (CDCl$_3$, TPPO): d −15.59 and −15.78. HPLC (35:65 CH$_3$CN/H$_2$O [0.1% TFA]): 8.667 min, 92%. ESI MS (high resolution): Calculated for C$_{19}$H$_{35}$ClFN$_4$O$_{10}$P: m/z 555.1059 (M+H)$^+$; Found: 555.1059.

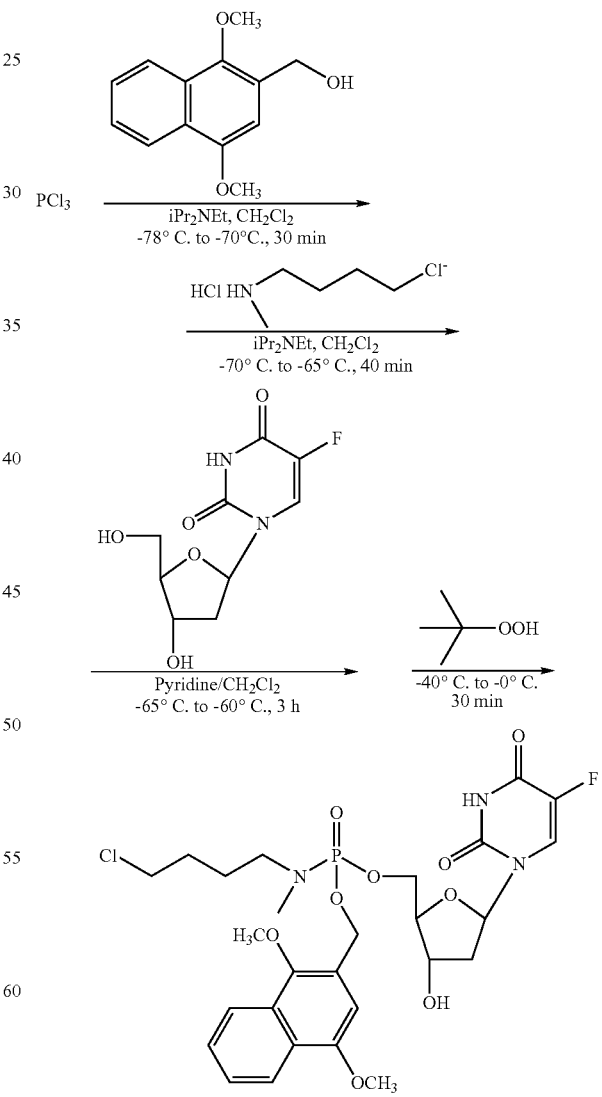

5-Fluoro-2'-deoxyuridyl 2-(1,4-dimethoxynapthyl) methyl N-methyl-N-(4-chlorobutyl) phosphoramidate (4)

Phosphoramidate 4 was prepared from phosphorus trichloride (2M in $CH_2Cl_2$; 0.41 mL; 0.812 mmol), 1,4-dimethoxy-2-hydroxymethylnapthalene (177 mg, 0.823 mmol), N-methyl-N-(4-chlorobutyl)amine hydrochloride (128 mg, 0.812 mmol), 5-fluoro-2'-deoxyuridine (100 mg, 0.406 mmol) and t-butylhydroperoxide (4.6M in decane; 0.23 mL) as described above for compound 3. Column chromatography of the crude product (1:1 $CH_2Cl_2$/acetone) afforded 4 (134 mg; 52%) as a light orange foam.

$^1$H NMR ($CDCl_3$): d 8.22 (dd, 1H); 8.04 (dd, 1H); 7.74 and 7.66 (d, 1H, J=6.23 & 6.39); 7.55 (m, 2H); 6.83 (s, 1H); 6.16 (m, 1H); 5.26 (m, 2H); 4.51 (m, 1H); 4.23 (m, 2H); 4.05 (m, 1H); 3.99 (s, 3H); 3.93 (s, 3H); 3.50 (m, 2H); 3.08 (m, 2H); 2.65 (d, 3H, J=9.70 Hz); 2.42 (m, 2H); 1.66 (m, 4H). $^{31}$P NMR ($CDCl_3$, TPPO): d −12.82 and −12.90 HPLC (50:50 $CH_3CN/H_2O$ [0.1% TFA]): 7.017 min; 95%. FAB MS (high resolution): Calculated for $C_{27}H_{34}ClFN_3O_4P$: m/z 630.1784 $(M+H)^+$; Found: 630.1760.

5-Fluoro-2'-deoxyuridyl 2-(1,4-napthoquinonyl) methyl N-methyl-N-(4-chlorobutyl) phosphoramidate (5)

Ceric ammonium nitrate (225 mg, 0.41 mmol) in water (3 mL) was added dropwise over 15 min to a solution of 4 (100 mg, 0.16 mmol) in $CH_3CN$ (3 mL). The reaction was stirred at room temperature for 1 hour and extracted with $CHCl_3$ (3×). Combined the organic layers and dried over $Na_2SO_4$, concentrated under reduced pressure. Purified by silica gel chromatography (5% $MeOH:CHCl_3$) to give 5 (87.6 mg, 93%) as a yellow foam.

$^1$H NMR ($CDCl_3$): d 8.10 (m, 2H); 7.77 (m, 2H); 7.72 (m, 1H); 7.03 (s, 1H); 6.18 (m, 1H); 5.02 (m, 2H); 4.58 (m, 1H); 4.29 (m, 2H); 4.05 (m, 1H); 3.57 (m, 2H); 2.73 (d, 3H, J=10.07 Hz); 2.47 (m, 1H); 2.31 (m, 1H); 1.75 (m, 4H). $^{31}$P NMR ($CDCl_3$, TPPO): d −12.67 and −12.99. HPLC (50:50 $CH_3CN/H_2O$ [0.1% TFA]): 4.650 min; 100%. FAB MS (high resolution): Calculated for $C_{25}H_{28}ClFN_3O_9P$: m/z 600.1314 $(M+H)^+$; Found: 600.1327.

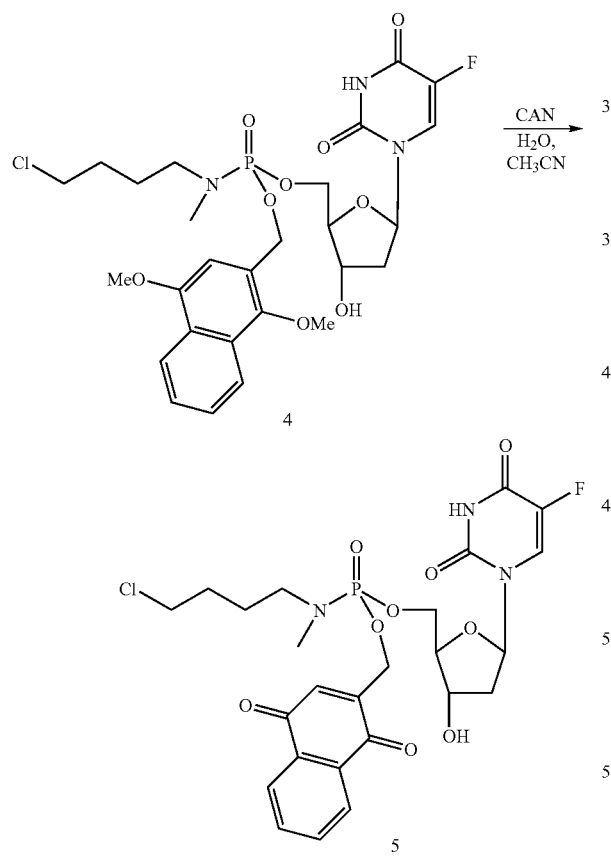

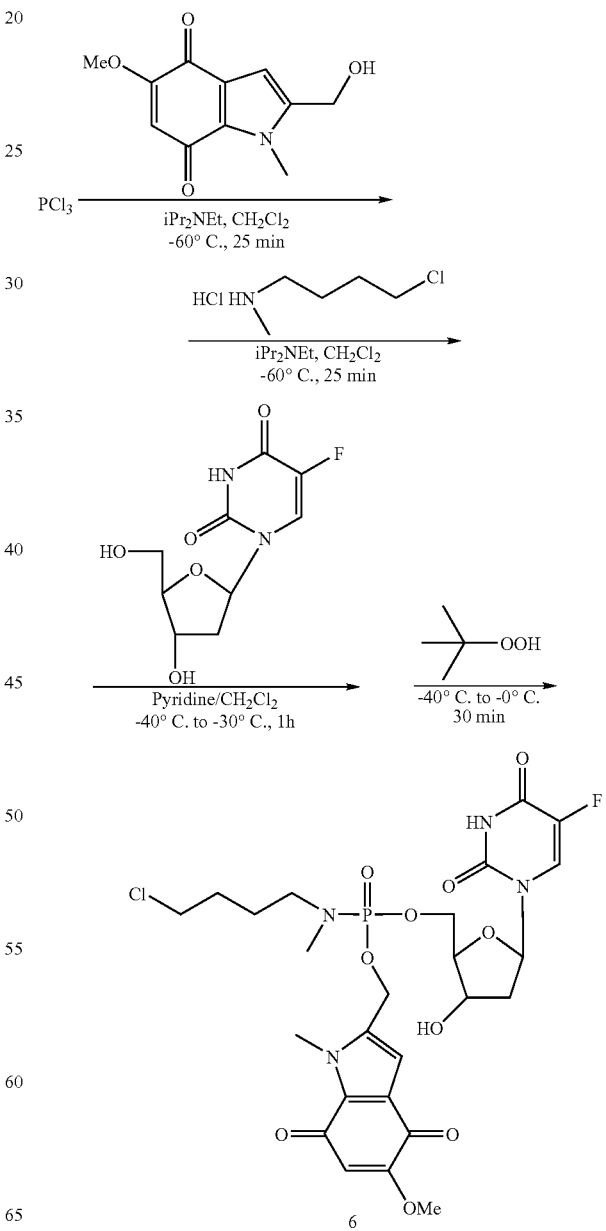

5-Fluoro-2'-deoxyuridyl 2-(5-methoxy-N-methylindoloquinone)methyl N-methyl-N-(4-chlorobutyl) phosphoramidate (6)

Phosphorus trichloride (2M in $CH_2Cl_2$; 0.13 mL; 0.258 mmol) was cooled to −60° C. under argon. 2-Hydroxymethyl-5-methoxy-N-methylindoloquinone (57 mg; 0.258 mmol) was dissolved in 6 mL of anhydrous $CH_2Cl_2$ plus 1 mL of anhydrous $CH_3CN$ and added to precooled $PCl_3$ followed by the dropwise addition of neat i-$Pr_2NEt$ (0.07 mL; 0.386 mmol). The reaction was stirred at −60° C. for 25 min. N-Methyl-N-(4-chlorobutyl)amine hydrochloride (40.7 mg; 0.258 mmol) was dissolved in 1 mL of anhydrous $CH_2Cl_2$ added to the reaction mixture followed by the dropwise addition of neat i-$Pr_2NEt$ (0.14 mL; 0.773 mmol), and stirred at −60° C. for 25 min. 5-Fluoro-2'-deoxyuridine (31.7 mg; 0.129 mmol) was co-evaporated with anhydrous pyridine, dissolved in 2 mL of anhydrous pyridine and cooled to −45° C. This solution of pyridine was titrated with the previously made reaction mixture until FUdR disappeared. The disappearance of FUdR was monitored by TLC using 30% methanol in chloroform. After 1 hour, the reaction was oxidized with t-butylhydroperoxide (4.6 M in decane; 0.06 mL) at −40° C. and stirred from −40° C. to 0° C. over 30 min. Saturated $NH_4Cl$ (3 mL) was added, separated the layers and the aqueous layer was extracted with $CHCl_3$ (5×5 mL). Combined organic layers and dried over $Na_2SO_4$ and concentrated under reduced pressure. The crude reaction mixture was passed through a plug of silica gel using 15% methanol in chloroform. Further purification by chromatography on silica gel (1:9 MeOH/$CHCl_3$) afforded 6 (33 mg; 41%) as a yellow-orange foam.

$^1$H NMR ($CDCl_3$): d 8.99 (br, 1H); 7.62 (m, 1H); 6.62 (d, 1H, J=3.76 Hz); 6.11 (1H, J=4.30); 5.64 (s, 1H); 4.95 (m, 2H); 4.46 (m, 1H); 4.13 (m, 2H); 3.95 (d, 3H, J=4.03 Hz); 3.86 (m, 1H); 3.76 (s, 3H); 3.47 (m, 2H); 3.95 (m, 2H); 2.58 (m, 3H); 2.41 (m, 1H); 2.11 (m, 1H); 1.65 (m, 4H). $^{31}$P NMR ($CDCl_3$, TPPO): d −14.65 and −14.71. HPLC (Gradient 0% to 70% $CH_3CN/H_2O$ [0.1% TFA] over 30 min): 20.32 min; 80%. FAB MS (high resolution): Calculated for $C_{25}H_{31}ClFN_4O_{10}P$: m/z 633.1529 $(M+H)^+$; Found: 633.1506.

N-allyloxycarbonyl Arabinosylcytosine (7)

Diallyl pyrocarbonate (86.8 mg, 0.452 mmol) was diluted in 1,4-dioxane (5 mL) and added to a solution of arabinosylcytosine (100 mg, 1.61 mmol) dissolved in dd$H_2O$ (1 mL) at room temperature. After the reaction mixture was refluxed for two hours in an oil bath, the solvent was removed under reduced pressure and co-evaporated the white residue with anhydrous pyridine (3×5 mL). Purified by silica gel chromatography (15% MeOH in $CHCl_3$) to give 7 (91 mg, 76% based on recovered starting material) as a white foam.

$^1$H NMR (DMSO$_6$): d 10.75 (br, 1H); 8.04 (d, 1H, J=7.51 Hz); 7.00 (d, 1 h, J=7.51 Hz); 6.04 (d, 1H, J=3.85 Hz); 5.95 (m, 1H); 5.46 (m, 1H); 5.39 & 5.25 (dd, 1H, J=1.47 & 35.34 Hz); 5.32 & 5.21 (dd, 1H, J=1.1 & 23.32 Hz), 5.11 (m, 1H); 4.62 (d, 2H, J=5.31 Hz); 4.04 (m, 1H); 3.91 (m, 1H); 3.81 (m, 1H); 3.60 (m, 2H).

HPLC (Gradient 0% to 70% $CH_3CN/H_2O$ [0.1% TFA] over 30 min): 12.18 min; 99%. ESI MS (low resolution): (M+H)=328 m/z; MW=327 for $C_{13}H_{17}N_3O_7$.

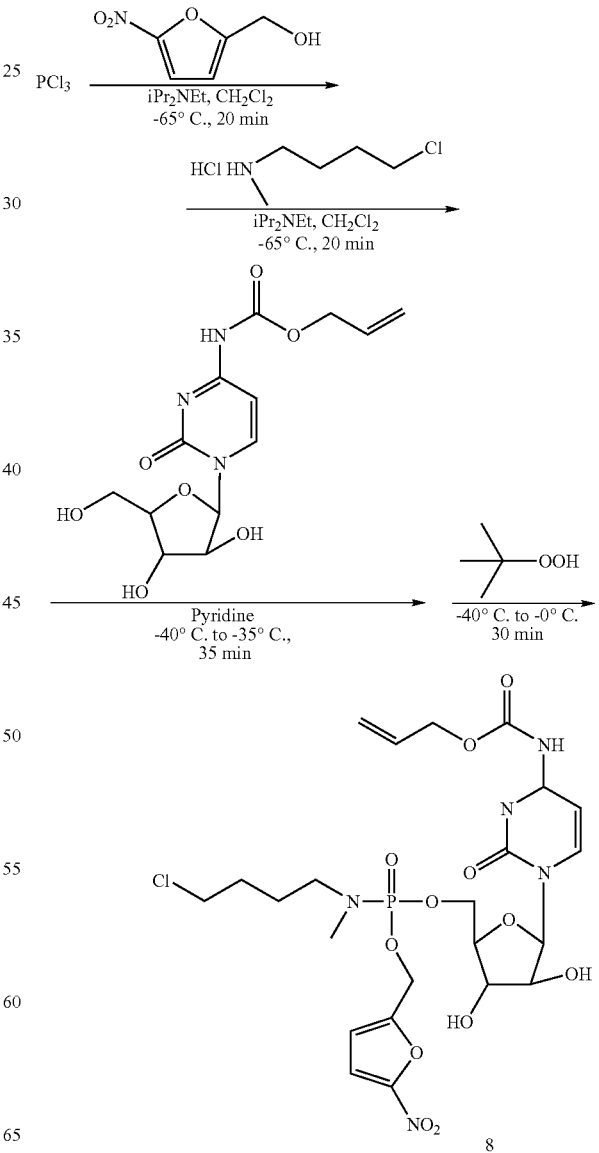

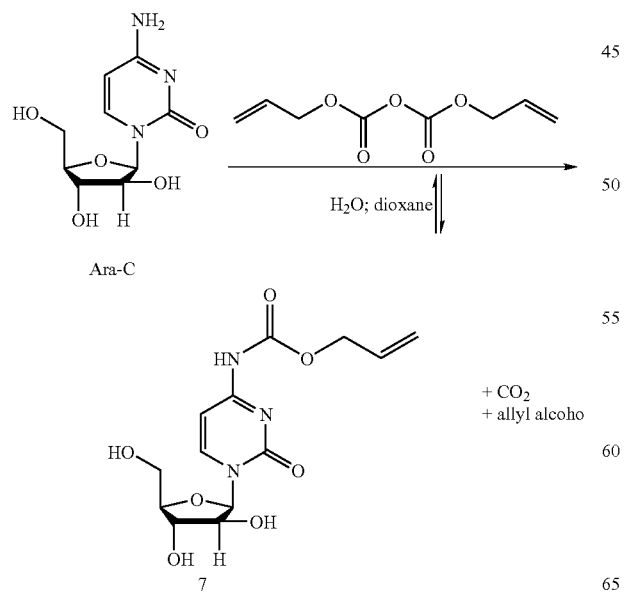

N-allyloxycarbonylarabinosylcytosyl 5-nitrofurfuryl N-methyl-N-(4-chlorobutyl) phosphoramidate (8)

Phosphoramidate 8 was prepared from phosphorus trichloride (2M in $CH_2Cl_2$; 1.14 mL; 2.28 mmol), 5-nitrofurfuryl alcohol (326 mg, 2.28 mmol), N-methyl-N-(4-chlorobutylamine hydrochloride (360 mg, 2.28 mmol), N-allyloxycarbonyl arabinosylcytosine (240 mg, 0.733 mmol) and t-butylhydroperoxide (4.6 M in decane; 0.48 mL) as described above for compound 6. Column chromatography of the crude product (10% methanol in $CHCl_3$) afforded 8 (227 mg; 50%) as a light yellow foam.

$^1$H NMR ($CDCl_3$): d 8.23 (d, 1H, J=7.33 Hz); 7.23 (d, 1H, J=1.33 Hz); 6.69 (m, 1H); 6.15 (1H); 5.91 (m, 1H); 5.34 (m, 3H); 5.02 (m, 2H); 4.55 (m, 4H); 4.23 (m, 2H); 3.55 (t, 2H, J=5.68 Hz); 3.03 (m, 2H); 2.67 (d, 3H, J=10.26 Hz); 1.73 (m, 4H). $^{31}$P NMR ($CDCl_3$, TPPO): d −15.54 and −15.76. HPLC (Gradient 0% to 70% $CH_3CN/H_2O$ [0.1% TFA] over 30 min): 20.01 min; 95%. ESI MS (high resolution): Calculated for $C_{23}H_{31}ClN_5O_{12}P$: m/z 636.1474 (M+H)$^+$; Found: 636.1474.

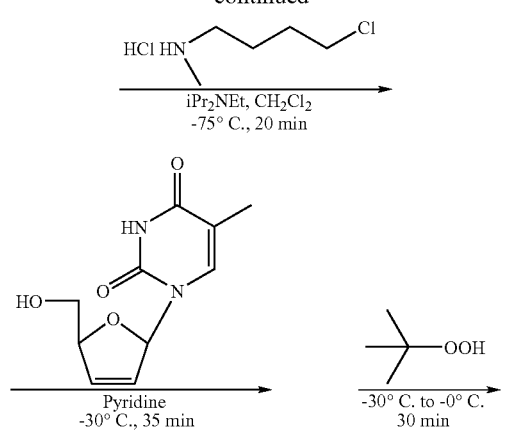

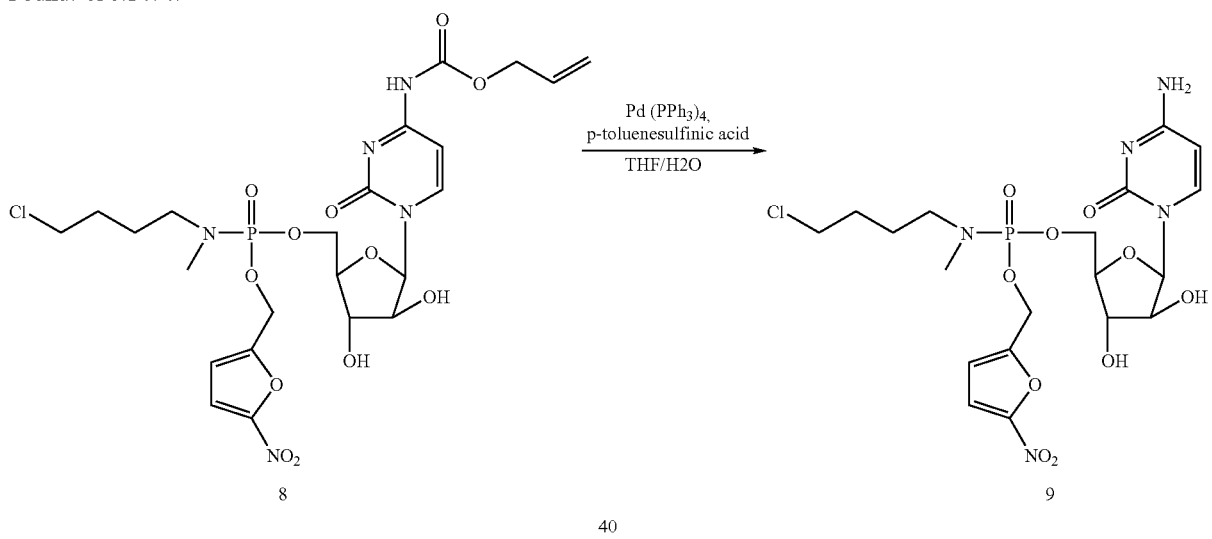

Arabinosylcytosyl 5-nitrofurfuryl N-methyl-N-(4-chlorobutyl) phosphoramidate Tetrakis(triphenyl phosphine)palladium (3.45 mg, 29.9 mmol) was added to a solution of phosphoramidate 8 (38 mg, 59.8 mmol) in THF (400 mL), followed by the addition of p-toluenesulfinic acid (11.71 mg, 65.7 mmol) in dd$H_2O$ (240 mL). The reaction mixture was allowed to stir at room temperature for 2.5 hours, after which time it was ran through a plug of silica gel (20% methanol in chloroform) to give a light yellow foam (25.1 mg, 76%).

$^1$H NMR ($CD_3OD$): d 7.85 (m, 2H); 7.49 (m, 1H); 6.89 (m, 1H); 6.57 (m, 1H); 5.95 (m, 1H); 5.11 (m, 2H); 4.19 (m, 5H); 3.66 (m, 2H); 3.11 (m, 2H); 2.72 (m, 3H); 1.79 (m, 4H). $^{31}$P NMR ($CD_3OD$, TPPO): d −14.18 and −14.37 HPLC (Gradient 0% to 70% $CH_3CN/H_2O$ [0.1% TFA] over 30 min): 21.43 min; 95%. ESI MS (high resolution): Calculated for $C_{19}H_{27}ClN_5O_{10}P$: m/z 552.1262 (M+H)$^+$; Found: 552.1251.

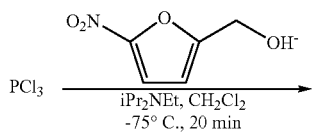

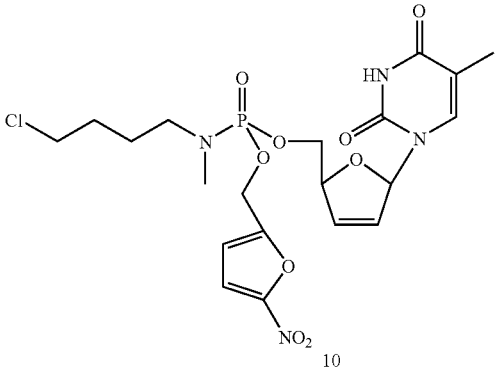

2',3'-Dideoxy-2',3'-didehydrothymidyl 5-nitrofurfuryl N-methyl-N-(4-chlorobutyl) phosphoramidate (10)

Phosphoramidate 10 was prepared from phosphorus trichloride (2M in $CH_2Cl_2$; 0.45 mL; 0.892 mmol); 5-nitrofurfuryl alcohol (128 mg, 0.892 mmol); N-methyl-N-(4-chlorobutylamine hydrochloride (141 mg, 0.892 mmol);

2',3'-dideoxy-2',3'-didehydrothymidyl (100 mg, 0.446 mmol) and t-butylhydroperoxide (4.6M in decane; 0.45 mL) as described above for compound 6. Column chromatography of the crude product (5% methanol in CHCl$_3$) afforded 10 (80.5 mg; 48%, based on recovered starting material) as a white foam.

$^1$H NMR (CDCl$_3$): d 8.19 (s, 1H); 7.29 (m, 1H); 7.19 (s, 1H); 6.98 (m, 1H); 6.66 (m, 1H); 6.34 (m, 1H); 5.91 (m, 1H); 4.99 (d, 3H, J=9.97 Hz); 4.16 (m, 2H); 3.56 (t, 2H, J=5.59 & 6.13 Hz); 3.06 (m, 2H); 2.63 (m, 3H); 1.87 (2s, 3H); 1.71 (m, 4H). $^{31}$P NMR (CDCl$_3$, TPPO): d −13.58 and −13.99. HPLC (Gradient 0% to 70% CH$_3$CN/H$_2$O [0.1% TFA] over 30 min): 22.75 & 23.18 min; 90%. ESI MS (high resolution): Calculated for C$_{20}$H$_{26}$ClN$_4$O$_9$P: m/z 533.1358 (M+H)$^+$; Found: 533.1350.

mmol); N-methyl-N-(4-chlorobutylamine hydrochloride (141 mg, 0.892 mm ol); 2',3'-dideoxy-2',3'-didehydrothymidyl (100 mg, 0.446 mmol) and t-butylhydroperoxide (4.6M in decane; 0.45 mL) as described above for compound 6. Column chromatography of the crude product (5% methanol in CHCl$_3$) afforded 11 (121 mg; 56%, based on recovered starting material) as a white foam.

$^1$H NMR (CDCl$_3$): d 8.24 (d, 1H, J=8.06 Hz); 8.05 (m, 2H); 7.54 (m, 2H); 7.19 (s, 1H); 6.98 (s, 1H); 6.84 (s, 1H); 6.31 (m, 1H); 5.58 (m, 1H); 5.24 (d, 2H, J=7.69 Hz); 4.98 (m, 1H); 4.15 (m, 2H); 4.98 (m, 6H); 3.50 (t, 2H, J=5.86 & 6.31 Hz); 3.04, m, 2H); 2.61 (m, 3H); 1.86 (s, 3H); 1.71 (m, 4H). $^{31}$P NMR (CDCl$_3$, TPPO): d −13.44 and −13.88. HPLC (Gradient 0% to 70% CH$_3$CN/H$_2$O [0.1% TFA] over 30 min): 28.08 & 28.30 min; 87%. ESI MS (low resolution): Calculated for C$_{28}$H$_{35}$ClN$_3$O$_8$P: 608 (M+H)$^+$; Found: 630 (Na adduct).

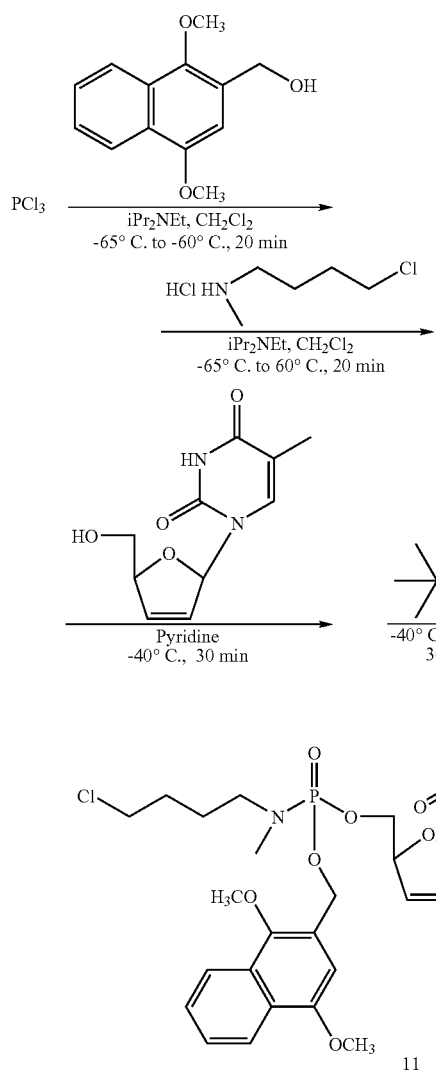

2',3'-Dideoxy-2',3'-didehydrothymidyl 2-(1,4-dimethoxynapthyl)methyl N-methyl-N-(4-chlorobutyl) phosphoramidate (11)

Phosphoramidate 11 was prepared from phosphorus trichloride (2M in CH$_2$Cl$_2$; 0.45 mL; 0.892 mmol); 1,4-dimethoxy-2-hydroxymethylnapthalene (195 mg, 0.892

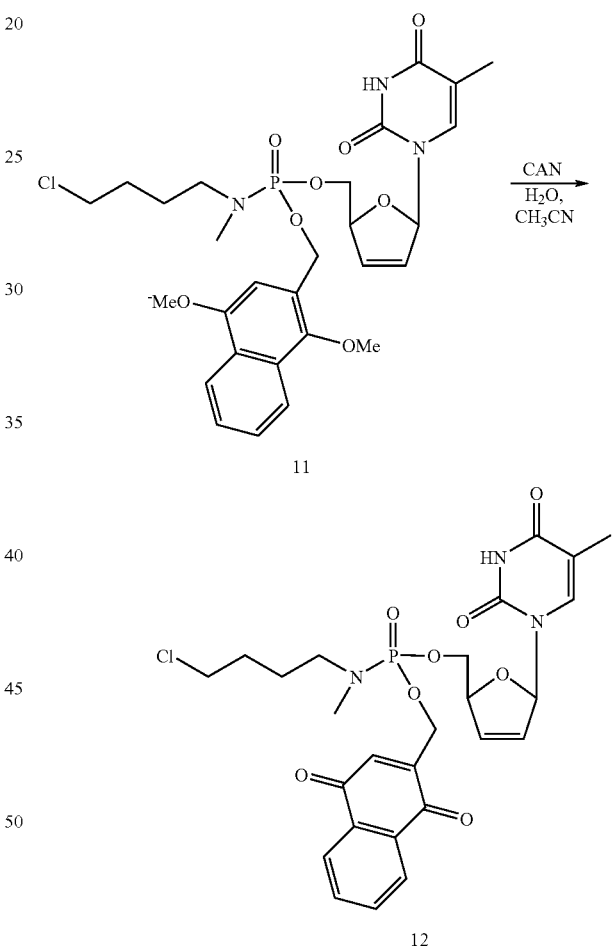

2',3'-Dideoxy-2',3'-didehydrothymidyl 2-(1,4-napthoquinonyl)methyl N-methyl-N-(4-chlorobutyl) phosphoramidate (12)

Ceric ammonium nitrate (225 mg, 0.411 mmol) in water (3 mL) was added dropwise over 15 min to a solution of 11 (100 mg, 0.164 mmol) in CH$_3$CN (3 mL). The reaction was stirred at room temperature for 1 hour and extracted with CHCl$_3$ (3×). Combined the organic layers and dried over Na$_2$SO$_4$, concentrated under reduced pressure. Purified by silica gel chromatography (5% MeOH:CHCl$_3$) to give 12 (78 mg, 82%) as a yellow foam.

$^1$H NMR (CDCl$_3$): d 8.09 (m, 2H); 8.01 (s, 1H); 7.79 (m, 2H); 7.17 (s, 1H); 6.99 (m, 2H); 6.35 (m, 1H); 5.93 (m, 1H); 5.00 (m, 3H); 4.24 (m, 2H); 3.56 (t, 2H, J=5.86 & 6.31 Hz); 3.11 (m, 2H); 2.71 (d, 3H, J=10.07 Hz); 1.90 (s, 3H); 1.74 (m, 4H). $^{31}$P NMR (CDCl$_3$, TPPO): d −13.49 and −13.84. HPLC (Gradient 0% to 70% CH$_3$CN/H$_2$O [0.1% TFA] over 30 min): 24.82 & 25.02; 95%. FAB MS (high resolution): Calculated for C$_{25}$H$_{29}$ClN$_3$O$_8$P: m/z 600.1279 (Na$^+$ adduct); Found: 600.1297 (Na$^+$ adduct).

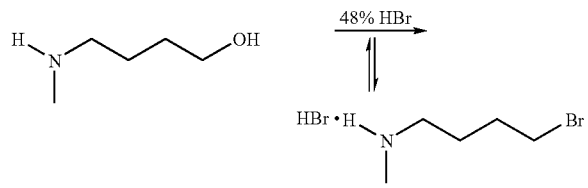

N-methyl-N-(4-bromobutyl)amine hydrobromide

Hydrobromic acid (20 mL, 0.38 mmol, 48% by wt) was added slowly with stirring to N-methyl-N-butan-4-ol (4.0 g, 0.39 mmol) at 0° C. The reaction mixture was heated to reflux for 2 hours. A distillation apparatus was attached and 10 mL of distillate was collected, an additional 10 mL (0.18 mmol) of 48% HBr was added. After refluxing for 4 hours, 10 mL were distilled off, an additional 10 mL of 48% HBr (0.18 mmol) were added and the reaction was refluxed overnight. The reaction mixture was then ditilled (~20 mL of distillate) and the still pot residue was poured into acetone at −78° C. A white precipitate formed and was collected by filtration (4.24 g, 44%).

$^1$H NMR: CDCl$_3$: d 9.08 (s, 1H); 3.46 (t, 2H, J=5.95 Hz); 3.04 (m, 2H); 2.72 (t, 3H, J=5.67 Hz); 2.05 (m, 4H); 1.70 (s, 1H). D$_2$O: 2.84 (t, 2H, J=6.13 Hz); 2.39 (t, 2H, J=7.32 Hz); 2.04 (s, 3H); 1.23 (m, 4H).

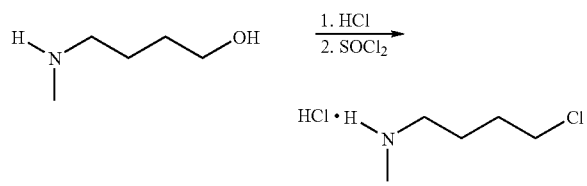

N-methyl-N-(4-chlorobutyl)amine hydrochloride

To a solution of N-methyl-N-butan-4-ol (2.0 g, 19.38 mmol) in 10 mL of CH$_2$Cl$_2$ stirring at room temperature, HCl gas was bubbled until it turned litmus paper red (pH=2). The reaction mixture was cooled to 0° C., thionyl chloride (1.41 mL, 19.38 mmol) was added dropwise and the reaction was stirred at room temperature overnight. The solvent was removed under reduced pressure to give a white solid (2.9 g, 95%).

$^1$H NMR: CDCl$_3$: d 8.79 (s, 1H); 3.59 (t, 2H, J=5.95); 2.97 (m, 2H); 2.70 (s, 3H); 2.06 (m, 2H); 1.95 (m, 2H); 1.63 (s, 1H). D$_2$O: d 3.50 (m, 2H); 2.75 (m, 2H); 2.55 (s, 3H); 1.70 (m, 4H). CI MS (low resolution): (M+H)$^+$=122 m/z; MW=121 for C$_5$H$_{12}$NCl.

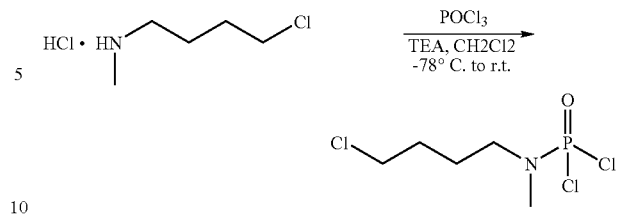

N-methyl-N-(4-chlorobutyl) phosphoramidic dichloride

N-methyl-N-(4-chlorobutyl)amine hydrochloride (2.0 g, 12.73 mmol) was dissolved in 20 mL of anhydrous CH$_2$Cl$_2$ and cooled to −40° C. Phosphorous oxycloride (1.2 mL, 12.73 mmol) was added neat followed by the drop wise addition of triethyl amine (3.6 mL, 25.46 mmol) in 5 mL of CH$_2$Cl$_2$. Warmed reaction to 0° C. and slowly to room temperature. Allowed reaction to stir at room temperature for 6 hours. The reaction mixture was poured over ice, added saturated ammonium chloride and separated layers. Extracted water layer 3× with CH$_2$Cl$_2$, combined organic layers, dried over anhydrous sodium sulfate and concentrated under reduce pressure. Purified by silica gel flash chromatography (3:1 Hex/EtOAc) to yield a clear oil (2.57 g, 85%).

$^1$H NMR (CDCl$_3$): d 3.58 (t, 2H, J=5.95 Hz); 3.29 (m, 2H); 2.84 (d, 3H, J=15.93 Hz); 1.79 (m, 4H). $^{31}$P NMR (CDCl$_3$, TPPO): d −6.6.

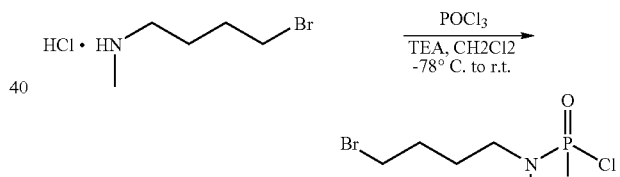

N-methyl-N-(4-bromobutyl) phosphoramidic dibromide

Used same precedure as described above (except that reaction was stirred overnight) with N-methyl-N-(4-bromobutyl)amine hydrobormide (2.0 g, 8.09 mmol). Purified using flash silica gel chromatography (3:1 Hex/EtOAc) to yield a clear oil (2.0 g, 92%).

$^1$H NMR (CDCl$_3$): d 3.46 (t, 2H, J=6.05 Hz); 3.30 (q, 2H); 2.85 (d, 3H, J=16.11 Hz); 1.88 (m, 4H). $^{31}$P NMR (CDCl$_3$, TPPO): d −6.75.

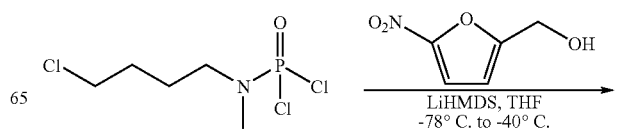

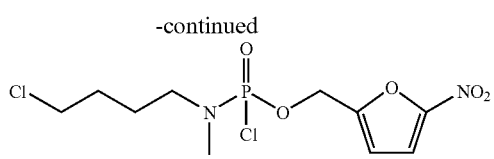

5-Nitro-2-furylmethyl N-methyl-N-(4-chlorobutyl) phosphoramidic chloride

Tetrahydrofurfuryl alcohol (240 mg, 1.68 mmol) was dissolved in 10 mL of anhydrous THF and cooled to –78° C. Lithium hexamethyl disilazane (1.84 mL, 1.84 mmol) was added dropwise and the reaction was stirred for 10 min at –78° C. A solution of phophoramidic dichloride (400 mg, 1.68 mmol) in 10 mL of anhydrous THF was added dropwise to the reaction mixture. Warmed the reaction slowly from –78° C. to –60° C. and allowed to stir at –60° C. for 1 hour. Quenched with saturated NH$_4$Cl, separated layers, extracted water layer 3× with EtOAc. Organic layers were combined, dried over anhydrous sodium sulfate and concentrated under reduced pressure. Purified using flash silica gel chromatography (10:1 CH$_2$Cl$_2$/Acetone) to yield a light brown oil (320 mg, 55%).

$^1$H NMR (CDCl$_3$): d 7.29, (d, 1H, J=3.66 Hz); 6.72 (d, 1H, J=3.66 Hz); 5.14 (dd, 2H); 3.56 (t, 2H, J=5.86); 3.20 (m, 2H); 2.71 (d, 3H, J=13.58 Hz), 1.79 (m, 4H). $^{31}$P NMR (CDCl$_3$, TPPO): d –7.88.

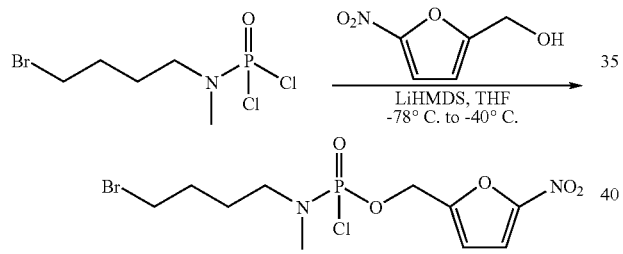

5-Nitro-2-furylmethyl N-methyl-N-(4-bromobutyl) phosphoramidic chloride

Procedure same as described as above starting with nitrofurfuryl alcohol (245 mg, 1.78 mmol) and phosphoramidic dichloride (500 mg, 1.78 mmol). Purified using flash silica gel chromatography (10:1, CH$_2$Cl$_2$/Acetone) to yield a light brown oil (360 mg, 52%).

$^1$H NMR (CDCl$_3$): d 7.29, (d, 1H, J=3.67 Hz); 6.72 (d, 1H, J=3.66 Hz); 5.14 (dd, 2H); 3.43 (t, 2H, J=6.32); 3.19 (m, 2H); 2.72 (d, 3H, J=13.73 Hz), 1.79 (m, 4H). $^{31}$P NMR (CDCl$_3$, TPPO): d –7.88.

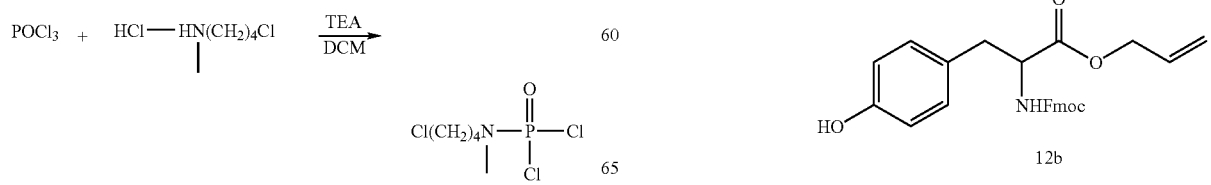

Synthesis of Phosphoramidic Dichloride.

Diisopropyl amine (8.82 mL, 50.61 mmol) was diluted with 20 mL of dry dichloromethane and added slowly to a pre-cooled solution of POCl$_3$ (2.36 mL, 25.31 mmol) and N-methyl-4-chlorobutyl amine hydrochloride (4 g, 24.31 mmol) in 40 mL of dry dichloromethane at –20° C. Reaction mixture was stirred for 3.5 hours letting it warm up gradually to 10° C. Reaction mixture was quenched with saturated ammonium chloride and extracted with dichloromethane. Organic layers were collected, washed with brine, dried over MgSO$_4$ and evaporated to dryness to yield a yellow liquid. Crude product was chromatographed using a mixture of 3:1 Hexanes/EtOAc to yield phosphoramidic dichloride as a clear liquid (5.07 g, 84% yield).

$^1$H NMR (CDCl$_3$, TMS) d: 3.59 (t, 2H), 3.29 (m, 2H), 2.85 (d, 3H, j=16.11 Hz), 1.80 (m, 4H) ppm.

$^{31}$P NMR (CDCl$_3$, TPPO) d: –6.63 ppm.

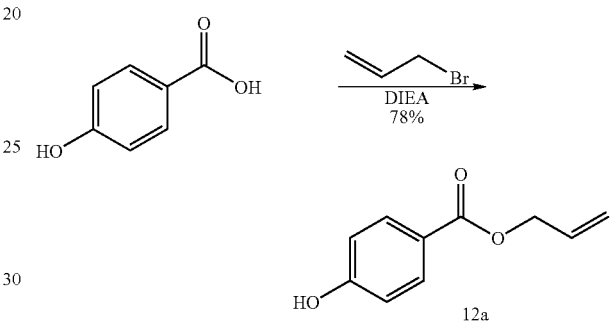

Synthesis of 1-propenyl benzoate 12a.

Diisopropyl amine (6.31 mL, 36.20 mmol) was added neat to a suspension of 4-hydroxybenzoic acid (5 g, 36.20 mmol) in 86 mL of allyl bromide. Reaction mixture was stirred at reflux for 2 hours and allowed to cool to room temperature. Excess allyl bromide was distilled off under reduced pressure and the remaining oil was diluted in EtOAc and washed with water, brine, dried over MgSO$_4$ and evaporated to dryness to yield a yellow oil. Crude product was chromatographed using a mixture of 10:1 CHCl$_3$/EtOAc to yield the benzoate ester (5.03 g, 78% yield) as a white solid.

$^1$H NMR (CDCl$_3$, TMS) d: 7.99 (d, 2H, j=8.79 Hz), 6.86 (d, 2H, j=8.79 Hz); 6.0 (m, 1H), 5.30 (m, 2H), 4.80 (d, 2H, j=5.68 Hz). HPLC (50:50 CH$_3$CN/H$_2$O-0.1% TFA): 6.17 min (97.2%). MS (ESI) m/z: 179 (M+H) GCMS m/z: 179 (M+H).

Synthesis of 1-propenyl ester 12b.

Ester 12b was synthesized as described for 12a and was obtained as a white solid (78% yield).

$^1$H NMR (CDCl$_3$, TMS) d: 7.77 (d, 2H, j=7.41 Hz), 7.56 (d, 2H, j=7.41 Hz), 7.43–7.28 (m, 4H), 6.96 (d, 2H, j=8.28 Hz), 6.73 (d, 2H, j=8.28 Hz), 5.94–5.80 (m, 1H), 5.35–5.24 (m, 3H), 4.91 (s, 1H), 4.62 (m, 3H), 4.48–4.31 (m, 2H), 4.20 (t, 1H), 3.06 (t, 2H). HPLC (50:50 CH$_3$CN/H$_2$O-0.1% TFA): 11.75 min (99.99%)

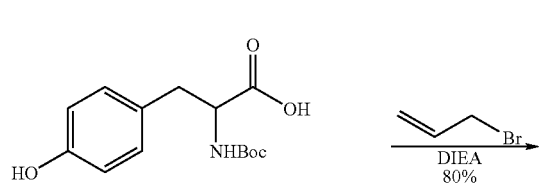

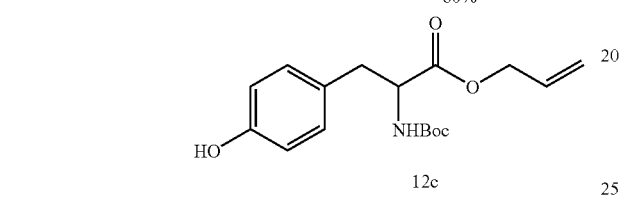

Synthesis of 1-propenyl ester 12c.

Ester 12c was synthesized as described for 12a and obtained as white solid (80% yield).

$^1$H NMR (CDCl$_3$, TMS) d: 6.99 (d, 2H, j=8.42 Hz), 6.73 (d, 2H, j=8.42 Hz), 5.84 (m, 1H), 5.27 (m, 2H), 4.60 (d, 2H, j=5.86 Hz), 3.02 (m, 1H), 1.42 (s, 9H). HPLC (30:70 CH$_3$CN/H$_2$O-0.1% TFA): 8.95 min (97%).

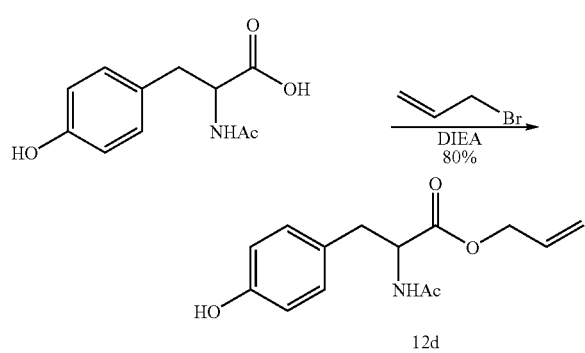

Synthesis of 1-propenyl ester 12d.

Ester 12d was synthesized as described for 12a and obtained as a white solid (80% yield).

$^1$H NMR (CDCl$_3$, TMS) d: 7.20–7.09 (m, 4H), 5.99–5.78 (m, 2H), 5.35–5.25 (m, 2H), 4.93–4.85 (m, 1H), 4.61 (d, 2H, j=5.86 Hz), 3.26–3.13 (m, 2H), 2.00 (s, 3H) ppm. HPLC (30:70, CH$_3$CN/H$_2$O-0.1% TFA): 5.63, 5.8 min. MS (ESI) m/z: 286 (M+Na).

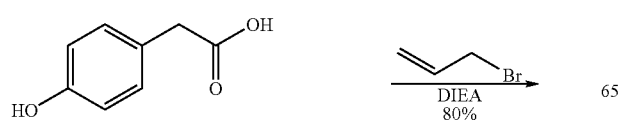

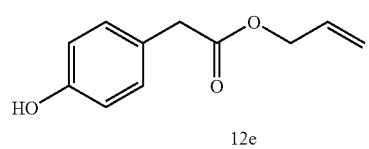

Synthesis of 1-propenyl ester 12e.

Ester 12e was synthesized as described for 12a and obtained as green oil.

$^1$H NMR (CDCl$_3$, TMS) d: 7.32–7.19 (m, 4H), 5.98–5.82 (m, 1H), 5.31–5.20 (m, 2H), 2H), 4.60 (d, 2H, j=5.68 Hz), 3.64 (s, 2H) ppm. HPLC (30:70, CH$_3$CN/H$_2$O-0.1% TFA): 4.33 min.

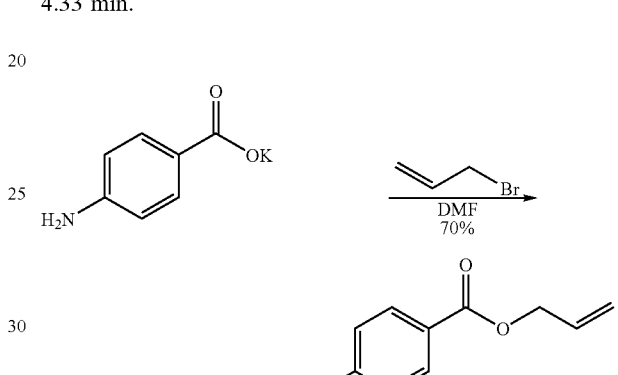

Synthesis of 1-propenyl ester 13

Allyl bromide (0.99 mL, 11.41 mmol) was added to a suspension of potassium p-aminobenzoate (2 g, 11.41 mmol) in 40 mL of DMF. Reaction was stirred overnight and then quenched with water and extracted several times with EtOAc. Organic extracts were combined, washed with brine, dried over MgSO$_4$ and evaporated to dryness to yield yellow liquid. Crude product was chromatographed using a mixture of 10:1 CHCl$_3$/EtOAc to yield 13 (2 g, 70% yield) as a light yellow solid.

$^1$H NMR (CDCl$_3$, TMS) d: 7.99 (d, 2H, j=8.7 Hz), 7.08 (d, 2H, j=8.7 Hz), 6.05–5.97 (m, 1H), 5.51–5.30 (m, 2H), 4.82–4.78 (m, 2H) ppm. HPLC (gradient 30–100% CH$_3$CN:H$_2$O-0.1% TFA over 35 min): 7.68 min MS (ESI) m/z: 178 (M+H), 200 (M+Na).

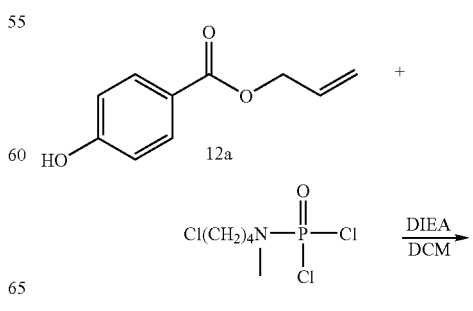

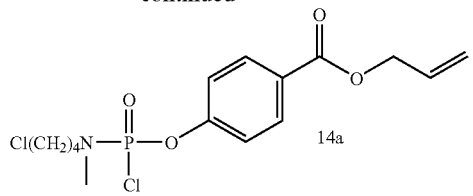

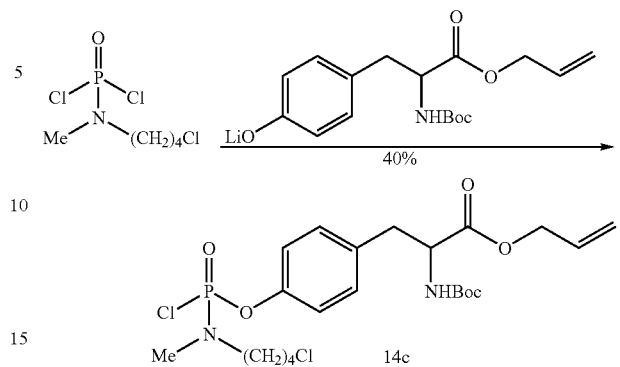

Synthesis of Phosphoramidic Monochloride 14a

Diisopropylethyl amine (0.3 mL, 1.68 mmol) was added neat to a pre-cooled solution of phosphoramidic dichloride (0.2 g, 0.84 mmol) and allyl ester 12a (0.15 g, 0.84 mmol) in 3 mL of dry DCM at −15° C. Reaction was stirred for 1 hr at −15° C. and 3 hours at −5° C. and quenched with saturated ammonium chloride. Layers were separated. Organic layer was then washed with brine, dried over $MgSO_4$ and evaporated to dryness to yield a yellow liquid. Crude product was chromatographed using a 10:1 mixture of $CHCl_3$/EtOAc to yield 14a as a clear liquid.

$^1$H NMR ($CDCl_3$, TMS) d: 8.10 (d, 2H, j=8.33 Hz), 7.34 (d, 2H, j=8.33 Hz), 6.09–5.98 (m, 1H), 5.45–5.28 (m, 2H), 4.84–4.81 (m, 2H), 3.57 (t, 2H), 3.35–3.17 (m, 2H), 2.84 (d, 3H, j=13.55), 1.82–1.79 (m, 4H) ppm. $^{31}$P NMR (TPPO) d: −13.07 ppm. HPLC (gradient 30–100%, $CH_3CN/H_2O$-0.1% TFA, over 35 min): 16.05 min.

Synthesis of Phosphoramidic Monochloride 14c.

14c was synthesized as described for 14b and obtained as light yellow oil.

$^1$H NMR ($CDCl_3$, TMS) d: 7.16 (m, 4H), 5.8 (m, 1H), 5.3 (m, 2H), 4.6 (d, 2H, j=5.68 Hz), 3.58 (t, 2H), 3.2 (m, 2H), 3.05 (m, 1H), 2.82 (d, 3H), 1.79 (m, 4H), 1.42 (s, 9H). $^{31}$P NMR ($CDCl_3$, TPO) d: −12.5 ppm. HPLC (gradient 30–100%, $CH_3CN/H_2O$-0.1% TFA, over 35 min): 9.83 min.

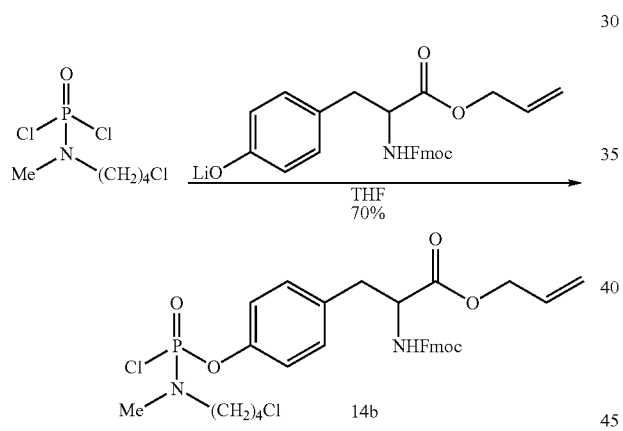

Synthesis of Phosphoramidic Monochloride 14b.

Phosphoramidic dichloride 11 (0.45 g, 1.89 mmol) was dissolved in 2 mL of dry THF and cannulated to a pre-cooled solution of 12b (0.84 g, 1.89 mmol) and LiHMDS (2.08 mmol) in 2 mL of dry THF at −20° C. Reaction was warmed up to 0° C. and stirred for 5 hours. Reaction was quenched with saturated ammonium chloride and extracted with ethyl acetate. Organic extracts were combined, washed with brine, dried over $MgSO_4$ and evaporated to dryness to yield yellow oil. Crude product was chromatographed using a 10:1 mixture of $CHCl_3$/EtOAc to yield 14b (0.85 g, 70% yield) as yellow oil.

$^1$H NMR ($CDCl_3$, TMS) d: 7.77 (d, 2H, j=7.42 Hz), 7.57 (d, 2H, j=7.42 Hz), 7.44–7.29 (m, 4H), 7.19–7.08 (m, 4H), 5.91–5.81 (m, 1H), 5.34–5.25 (m, 3H), 4.66–4.60 (m, 3H), 4.49–4.33 (m, 2H), 4.21 (t, 1H), 3.58 (t, 2H), 3.27–3.20 (m, 2H), 3.17–3.10 (m, 2H), 2.82 (d, 3H, j=13.54 Hz), 1.81–1.78 (m, 4H) ppm. $^{31}$P NMR ($CDCl_3$, TPPO) d: −12.64 ppm. HPLC (70:30 $CH_3CN/H_2O$-0.1% solution of TFA): 6.833 min. MS (ESI) m/z: 645/647 (M+H), 667/669 (M+Na).

Synthesis of Phosphoramidic Monochloride 14d.

14d was synthesized in a similar manner as 14a. The reaction mixture was stirred overnight to yield light yellow oil.

$^1$H NMR ($CDCl_3$, TMS) d: 7.20–7.09 (m, 4H), 5.99–5.78 (m, 2H), 5.35–5.25 (m, 2H), 4.93–4.85 (m, 1H), 4.61 (d, 2H, j=5.86 Hz), 3.58 (t, 2H), 3.26–3.13 (m, 4H), 2.83 (d, 3H, j=13.55 Hz), 2.00 (s, 3H), 1.96–1.75 (m, 4H) ppm. $^{31}$P NMR (TPPO) d: 12.71 MS (ESI) m/z: 465/467 (M+H).

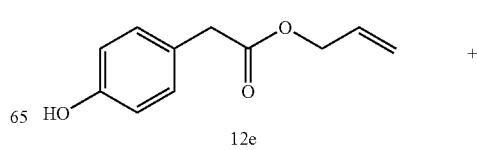

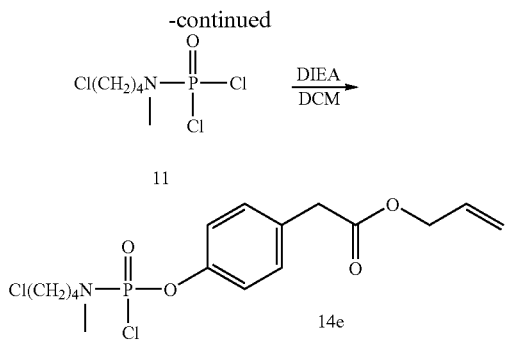

Synthesis of Phosphoramidic Monochloride 14e.

14e was synthesized in a similar manner as 13a.

$^1$H NMR (CDCl$_3$, TMS) d: 7.32–7.19 (m, 4H), 5.98–5.82 (m, 1H), 5.31–5.20 (m, 2H), 4.60 (d, 2H, j=5.68 Hz), 3.64 (s, 2H), 3.58 (t, 2H), 3.25–3.18 (m, 2H), 2.83 (d, 3H, j=13.55 Hz), 1.80–1.78 (in, 4H) ppm. $^{31}$P NMR (TPPO) d: −12.66 ppm. MS (ESI) m/z: 394/396 (M+H).

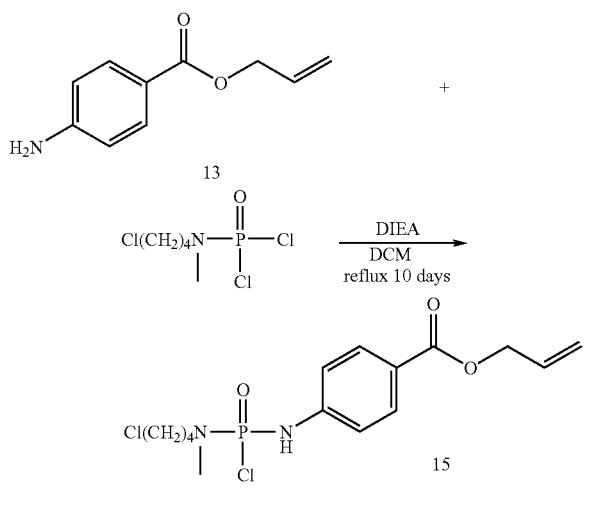

Synthesis of Phosphodiamidic Monochloride 15.

Diisopropylethyl amine (0.51 mL, 2.94 mmol) was added neat to a mixture of phosphoramidic dichloride 11 (0.7 g, 2.94 mmol) and allyl ester 13 (0.52 g, 2.94 mmol) in 10 mL of dry dichloromethane. Reaction was stirred at reflux for 10 days and allowed to cool down to room temperature, diluted with dichloromethane and quenched with saturated ammonium chloride. Layers were separated; organic layer was washed with brine, dried over MgSO$_4$ and evaporated to dryness to yield yellow oil. Crude product was chromatographed using a mixture of 10:1 CHCl$_3$/EtOAc to yield light green oil (0.22 g, 20% yield).

$^1$H NMR (CDCl$_3$, TMS) d: 7.99 (d, 2H, j=8.7 Hz), 7.08 (d, 2H, j=8.7 Hz), 6.05–5.97 (m, 1H), 5.57 (d, 1H, j=2.29 Hz), 5.51–5.30 (m, 2H), 4.82–4.78 (m, 2H), 3.54 (t, 2H), 3.36–3.13 (m, 2H), 2.74 (d, 3H, j=14.37 Hz), 1.87–1.64 (m, 4H) ppm. $^{31}$P NMR (TPPO) d: −11.28 ppm. HPLC (30–100%, CH$_3$CN/H$_2$O-0.1% TFA, over 35 min): 12.60 min. MS (ESI) m/z: 379/381 (M+H), 401/403 (M+Na).

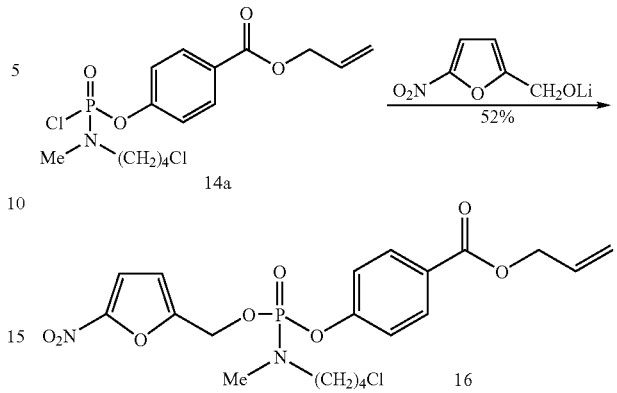

Synthesis of Phosphoramidate 16.

Phosphoramidic monochloride 14a (0.63 g, 1.21 mmol) was dissolved in 2 mL of dry THF and cannulated to a precooled solution of nitrofuryl alcohol (0.19 g, 1.33 mmol) and LiHMDS (1.46 mmol) in 2 mL of dry TBF at −78° C. Reaction was brought to −40° C. and stirred for 5.5 hours. Saturated ammonium chloride was added to the reaction mixture and extracted with ethyl acetate. Organic extracts were combined, washed with brine, dried over MgSO$_4$ and evaporated to dryness to yield dark oil. Crude product was chromatographed using a mixture of 10:1 CHCl$_3$/EtOAc to yield phosphoramidate 16 (0.30 g, 52% yield) as a dark orange oil.

$^1$H NMR (CDCl$_3$, TMS) d: 8.05 (d, 2H, j=8.6 Hz), 7.26 (m, 3H), 6.64 (d, 1H, j=3.48 Hz), 6.05 (m, 1H), 5.31 (m, 2H), 5.09 (d, 2H, j=9.15 Hz), 4.82 (d, 2H, j=5.49 Hz), 3.53 (t, 2H), 3.1 (m, 2H), 2.72 (d, 3H, j=10.25 Hz), 1.67 (m, 4H). $^{31}$P NMR (TPPO) d: −21.7 HPLC (60:40 CH$_3$CN/H$_2$O-0.1% solution of TFA): 7.117 min.

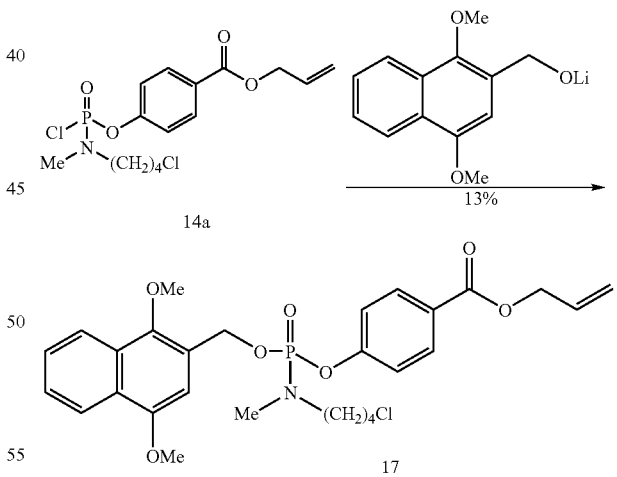

Synthesis of Phosphoramidate 17.

Phosphoramidate 17 was synthesized in a similar manner as described for 16.

$^1$H NMR (CDCl$_3$, TMS) d: 8.23 (d, 1H, j=7.14 Hz), 8.07–7.91 (m, 3H), 7.66–7.50 (m, 2H), 7.30 (d, 2H, j 8.7 Hz), 6.80 (s, 1H), 6.19–5.88 (m, 1H), 5.44–5.20 (m, 4H), 4.92–4.79 (m, 2H), 3.94 (s, 3H), 3.92 (s, 3H), 3.48 (t, 2H), 3.24–2.97 (m, 2H), 2.71 (d, 3H, j=10.25 Hz), 2.84–1.83 (m, 4H) ppm. $^{31}$P NMR (TPPO) d: −18.94 ppm. HPLC (70:30 CH$_3$CN/H$_2$O-0.01% TFA solution): 7.967 min MS (ESI) m/z: 584/586 (M+Na).

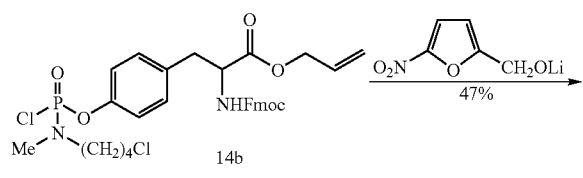

Synthesis of Phosphoramidate 18.

Phosphoramidate 18 was synthesized in a similar manner as described for 16.

$^1$H NMR (CDCl$_3$, TMS) d: 7.77 (d, 2H, j=7.42 Hz), 7.57 (d, 2H, j=7.42 Hz), 7.44–7.24 (m, 5H), 7.13–6.93 (m, 4H), 6.59 (d, 1H, j=3.67 Hz), 6.07–5.70 (m, 1H), 5.47–5.23 (m, 4H), 5.05 (d, 2H, j=9.16 Hz), 4.74–4.61 (m, 3H), 4.56–4.28 (m, 2H), 4.20 (t, 1H), 3.51 (t, 2H), 3.20–2.99 (m, 4H), 2.70 (d, 3H, j=10.34 Hz), 1.82–1.53 (m, 4H) ppm. $^{31}$P NMR (TPPO) d: −18.92 HPLC (70:30 CH$_3$CN/H$_2$O-0.1% solution of TFA): 6.12 min.

Synthesis of Phosphoramidate 19.

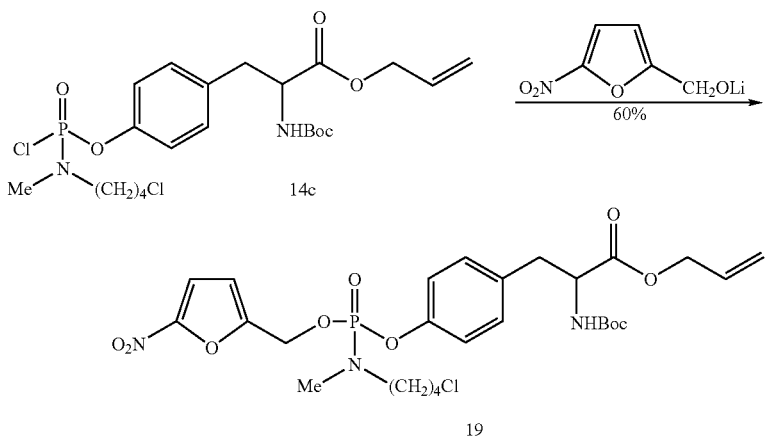

Phosphoramidate 19 was synthesized in a similar manner as 16.

$^1$H NMR (CDCl$_3$, TMS) d: 7.28 (d, 1H, j=3.66 Hz), 7.16 (m, 4H), 6.63 (d, 1H, j=3.66 Hz), 5.8 (m, 1H), 5.3 (m, 2H), 5.05 (d, 2H, j=8.98 Hz), 4.6 (d, 2H), 3.58 (t, 2H), 3.2 (m, 2H), 3.05 (m, 1H), 2.82 (d, 3H), 1.79 (m, 4H), 1.42 (s, 9H). $^{31}$P NMR (TPPO) d: −19.2 HPLC (60:40 CH$_3$CN/H$_2$O-0.1% TFA): 8.2 min.

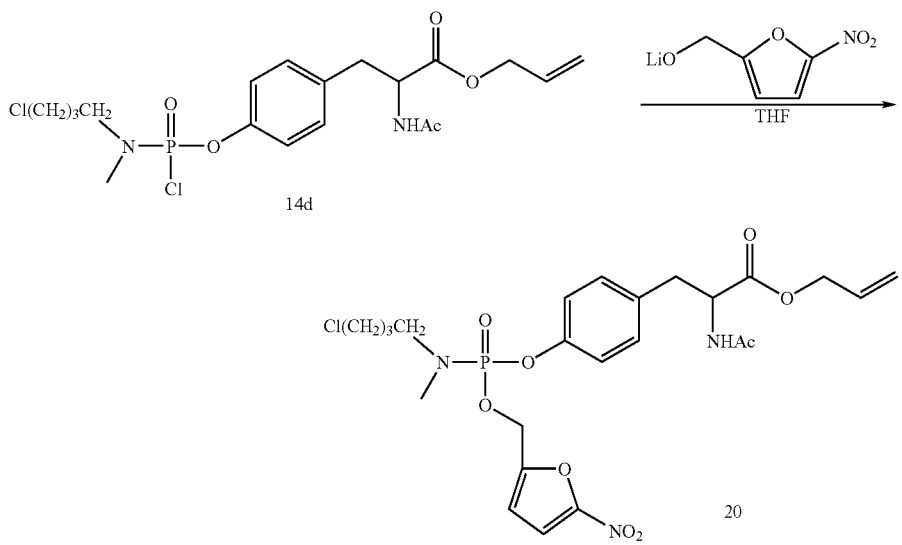

Synthesis of Phosphoramidate 20.

Phosphoramidate 20 was synthesized in a similar manner as described for 16.

$^1$H NMR (CDCl$_3$, TMS) d: 7.28 (d, 1H, j=3.75 Hz), 7.21–6.98 (m, 4H), 6.63 (d, 1H, j=3.75 Hz), 6.05–5.77 (m, 2H), 5.44–5.19 (m, 2H), 5.06 (d, 2H, j=9.15 Hz), 5.01–4.78 (m, 1H), 4.72–4.52 (m, 2H), 3.66–3.42 (m, 2H), 3.23–2.99 (m, 4H), 2.71 (d, 3H, j=10.34 Hz), 2.00 (s, 3H), 1.83–1.60 (m, 4H) ppm. $^{31}$P NMR (TPPO) d: −19.03 ppm. HPLC (gradient 30–100%, CH$_3$CN/H$_2$O-0.1% TFA, over 35 min): 15.70 min MS (ESI) m/z: 572/574 (M+H).

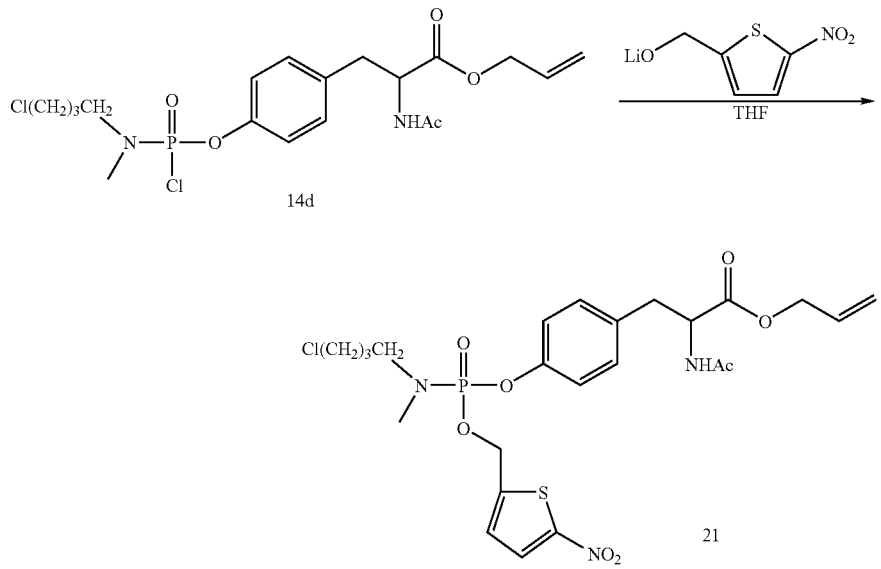

Synthesis of Phosphoramidate 21.

Phosphoramidate 21 was synthesized in a similar manner as described for 16.

$^1$H NMR (CDCl$_3$, TMS) d: 7.81 (d, 1H, j=4.12 Hz), 7.22–7.05 (m, 4H), 6.99 (d, 1H, j=4.12 Hz), 6.02–5.72 (m, 2H), 5.45–5.10 (m, 4H), 5.00–4.79 (m, 1H), 4.63–4.49 (m, 2H), 3.53 (t, 2H), 3.23–2.95 (m, 4H), 2.72 (d, 3H, j=10.35 Hz), 2.00 (s, 3H), 1.85–1.58 (m, 4H) ppm. $^{31}$P NMR (TPPO) d: −19.21 ppm. HPLC (gradient 30–100%, CH$_3$CN/H$_2$O-0.1% TFA, over 35 min): 17.20 min MS (ESI) m/z: 588/590 (M+H), 610/612 (M+Na).

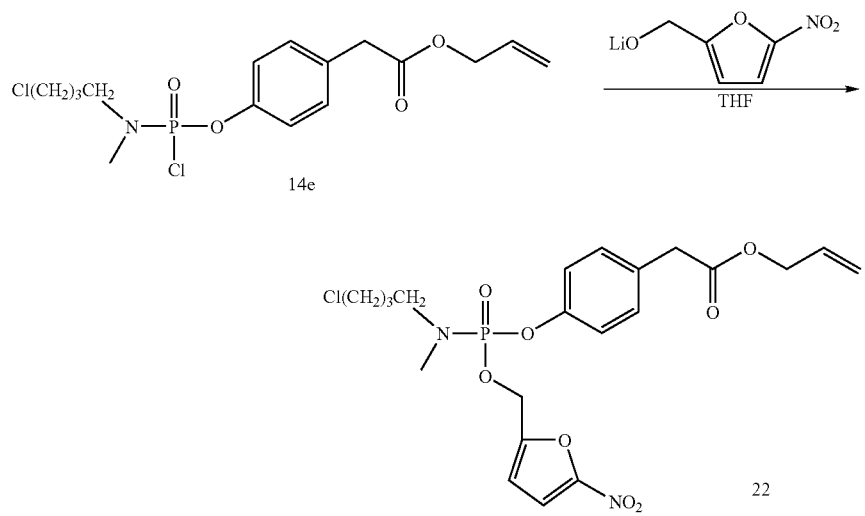

Synthesis of Phosphoramidate 22.

Phosphoramidate 22 was synthesized in a similar manner as described for 16.

$^1$H NMR (CDCl$_3$, TMS) d: 7.26–7.04 (m, 5H), 6.60 (d, 1H, j=3.58 Hz), 5.99–5.75 (m, 1H), 5.43–5.19 (m, 2H), 5.06 (d, 2H, j=9.16 Hz), 4.72–4.48 (m, 2H), 3.62 (s, 2H), 3.51 (t, 2H), 3.18–2.96 (m, 2H), 2.71 (d, 3H, j=10.26 Hz), 1.77–1.55 (m, 4H) ppm. $^{31}$P NMR (TPPO) d: −19.01 ppm. HPLC (30–100%, CH$_3$CN/H$_2$O-0.1% TFA, over 35 min): 15.50 min. MS (ESI) m/z: 501/503 (M+H), 523/525 (M+Na).

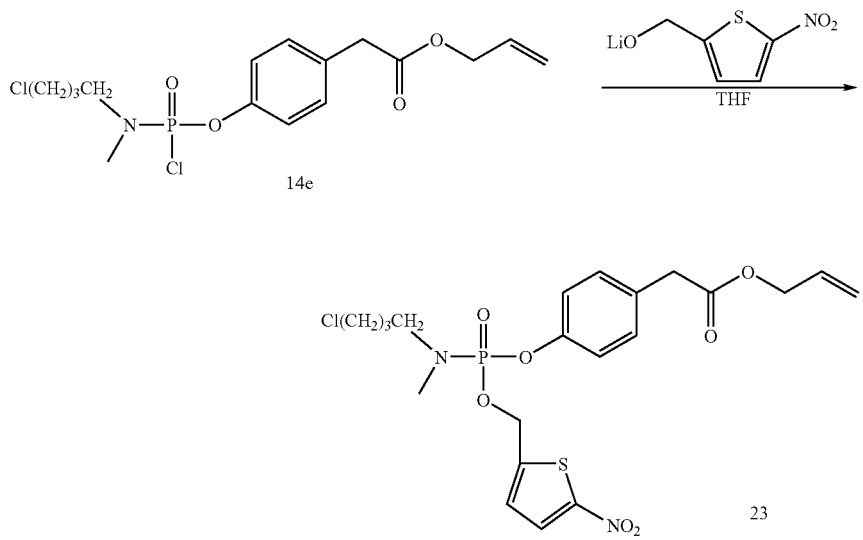

Synthesis of Phosphoramidate 23.

Phosphoramidate 23 was synthesized in a similar manner as described for 16.

$^1$H NMR (CDCl$_3$, TMS) d: 7.80 (d, 1H, j=4.12 Hz), 7.33–7.09 (m, 4H), 6.99 (d, 1H, j=4.12 Hz), 6.08–5.68 (m, 1H), 5.46–5.07 (m, 4H), 4.78–4.39 (m, 2H), 3.63 (s, 2H), 3.51 (t, 2H), 3.30–2.96 (m, 2H), 2.72 (d, 3H, j=10.34 Hz), 1.87–1.48 (m, 4H) ppm. $^{31}$P NMR (TPPO) d: −19.21 ppm. HPLC (gradient 30–100%, CH$_3$CN/H$_2$O-0.1% TFA, over 35 min): 20.17 min.

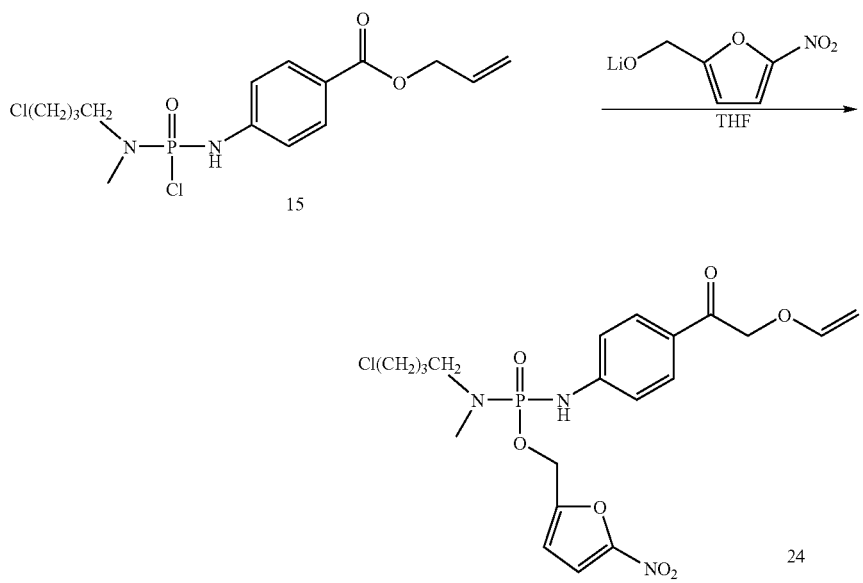

Synthesis of Phosphoramidate 24.

Phosphoradate 24 was synthesized in a similar manner as described for 16.

$^1$H NMR (CDCl$_3$, TMS) d: 7.96 9d, 2H, j=8.6 Hz), 7.26 (d, 1H, j=3.67 Hz), 6.99 (d, 2H, j=8.6 Hz), 6.65 (d, 1H, j=3.67 Hz), 6.16–5.84 (m, 1H), 5.51–5.19 (m, 3H), 5.09 (d, 2H, j=9.43 Hz), 4.92–4.73 (m, 2H), 3.52 (t, 2H), 3.22–2.99 (m, 2H), 2.69 (d, 3H, j=10.53 Hz), 1.85–1.61 (m, 4H) ppm. $^{31}$P NMR (TPPO) d: −15.60 ppm HPLC (gradient 30–100%, CH$_3$CN/120–0.1% TFA, over 35 min): 12.60 min. MS (ESI) m/z: 486/488 (M+H), 508/510 (M+Na).

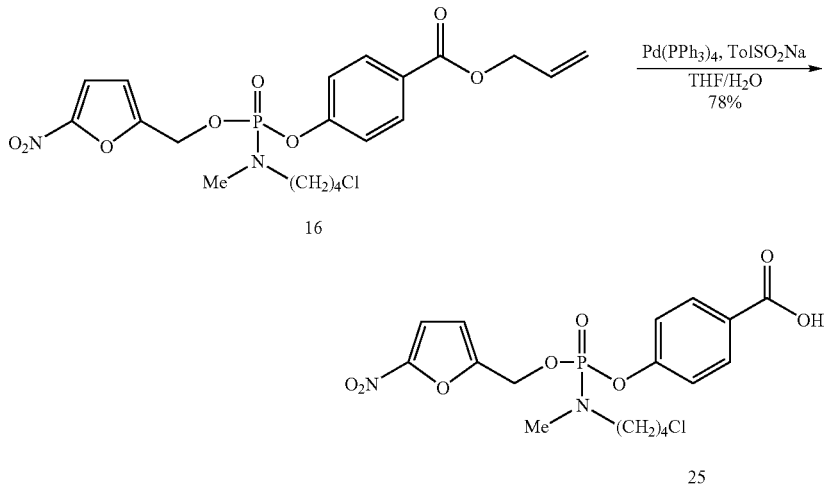

16

25

Synthesis of Phosphoramidate 25.

TolSO$_2$Na (0.29 g, 1.61 mmol) was dissolved in 2.5 mL of water and added to a solution of phosphoramidate 16 (0.71 g, 1.47 mmol) and Pd(PPh$_3$)$_4$ (0.08 g, 73.41 mmol) in 6 mL of TBF. Reaction was stirred for 30 minutes at room temperature. Diethyl ether was added to the reaction mixture and washed several times with water. Aqueous extracts were combined, washed with ether, acidified to pH 3 with 2% HCl and extracted with EtOAc. Organic extracts were combined, washed with brine, dried over MgSO$_4$ and evaporated to dryness to yield phosphoramidate 25 (0.51 g, 78% yield) as orange foam.

$^1$H NMR (CDCl$_3$, TMS) d: 8.08 (d, 2H, j=8.6 Hz), 7.31 (m, 3H), 6.66 (d, 1H, J=3.67 Hz), 5.11 (d; 2H, j=9.16 Hz), 3.53 (t, 2H), 3.13 (m, 2H), 2.74 (d, 3H, j=10.44 Hz), 1.7 (m, 4H). $^{31}$P NMR (TPPO) d: −20.4 HPLC (60:40 CH$_3$CN/H$_2$O-0.1% solution of TFA): 4.017 min.

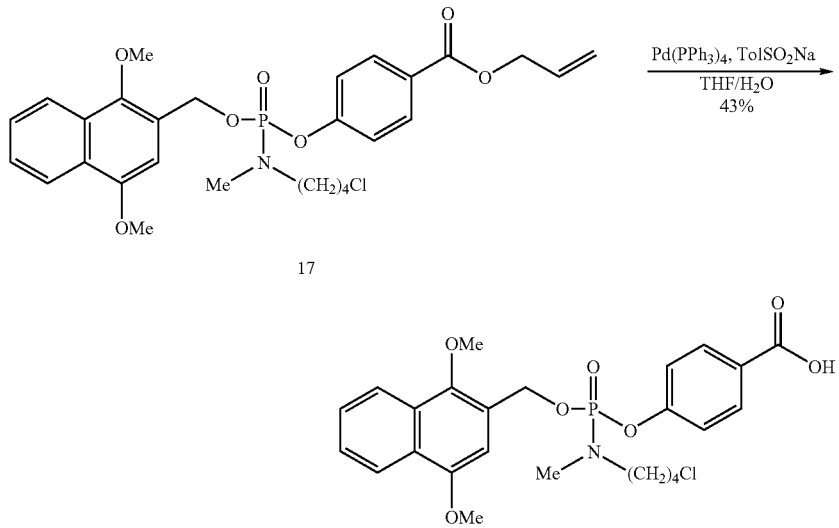

17

26

Synthesis of Phosphoramidate 26.

Phosphoramidate 26 was synthesized in a similar manner as described for 25.

$^1$H NMR (CDCl$_3$, TMS) d: 8.32–8.22 (m, 1H), 8.13–7.98 (m, 3H), 7.64–7.45 (m, 2H, 7.33 (d, 2H, j=8.7 Hz), 6.81 (s, 1H), 5.35 (d, 2H, j=8.05 Hz), 3.95 (s, 3H), 3.93 (s, 3H), 3.49 (t, 2H), 3.25–2.97 (m, 2H), 2.73 (d, 3H, j=10.25 Hz), 1.80–1.52 (m, 4H) ppm. $^{31}$P NMR (TPPO) d: −18.99 ppm HPLC (gradient 30–100%, CH$_3$CN/H$_2$O-0.1% TFA, over 35 min): 18.60 min. MS (ESI) m/z: 544/546 (M+Na).

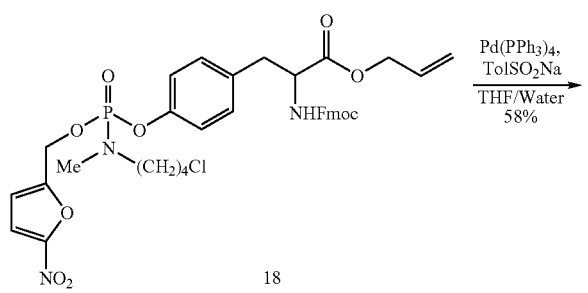

Synthesis of Phosphoramidate 27.

Phosphoramidate 27 was synthesized in a similar manner as described for 25.

$^1$H NMR (CDCl$_3$, TMS) d: 7.77 (d, 2H, j 7.23 Hz), 7.58 (d, 2H, j=7.23 Hz), 7.43–7.23 (m, 5H), 7.18–6.89 (m, 4H), 6.67–6.47 (m, 1H), 5.48–5.30 (m, 1H), 5.18–4.97 (m, 2H), 4.79–4.07 (m, 4H), 3.60–3.37 (m, 2H), 3.27–2.98 (m, 4H), 2.82–2.59 (m, 3H), 1.79–1.56 (m, 4H) ppm. $^{31}$P NMR (TPPO) d: −19.44, −19.63 ppm. HPLC (gradient 30–100%, CH$_3$CN/H$_2$O-0.1% TFA, over 35 min): 17.93 min.

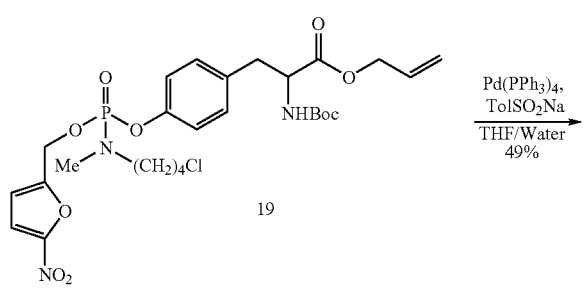

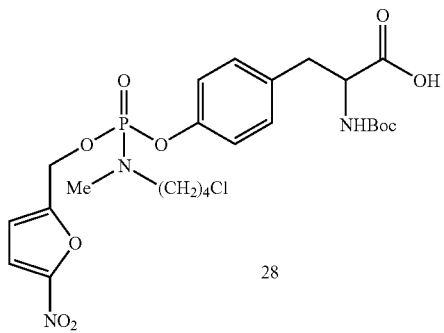

Synthesis of Phosphoramidate 28.

Phosphoramidate 28 was synthesized in a similar manner as described for 25.

$^1$H NMR (CDCl$_3$, TMS) d: 7.28 (d, 1H, j=3.66 Hz), 7.16 (m, 4H), 6.63 (d, 1H, j=3.66 Hz), 5.05 (d, 2H, j=8.98 Hz), 3.58 (t, 2H), 3.2 (m, 2H), 3.05 (m, 1H), 2.82 (d, 3H), 1.79 (m, 4H), 1.42 (s, 9H). $^{31}$P NMR (TPPO) d: −19.2 ppm. HPLC (60:40 CH$_3$CN/H$_2$O-0.1% TFA): 4.65 min.

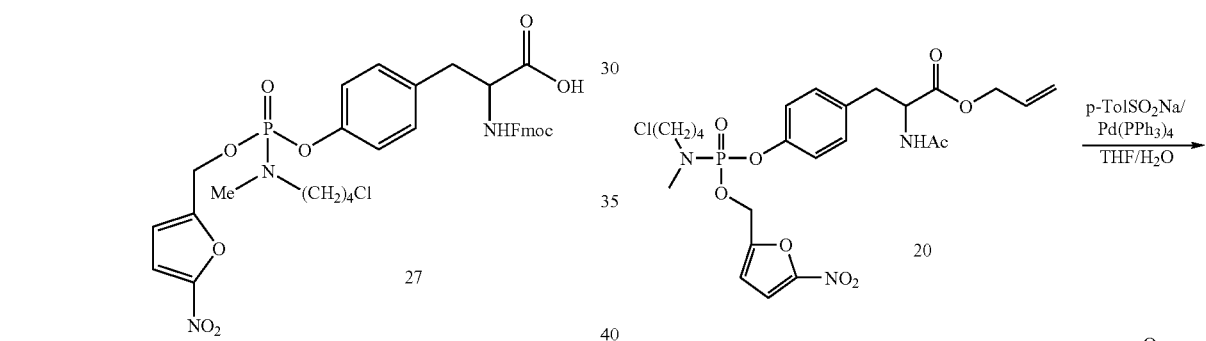

Synthesis of Phosphoramidate 29.

Phosphoramidate 29 was synthesized in a similar manner as described for 25.

$^1$H NMR (CDCl$_3$, TMS) d: 7.30–7.25 (m, 1H), 7.23–6.83 (m, 4H), 6.80–6.47 (m, 1H), 5.09 (d, 2H, j=9.25 Hz), 5.01–4.59 (m, 2H), 3.76–3.33 (m, 2H), 3.36–2.98 (m, 4H), 2.98–2.55 (m, 3H), 2.14–1.77 (d, 3H), 1.89–1.55 (m, 4H) ppm. $^{31}$P NMR (TPPO) d: −19.25, −19.43 ppm. HPLC (gradient 30–100%, CH$_3$CN/H$_2$O-0.1% TFA, over 35 min): 11.68 min. MS (ESI) m/z: 554/556 (M+Na), 532/534 (M+H).

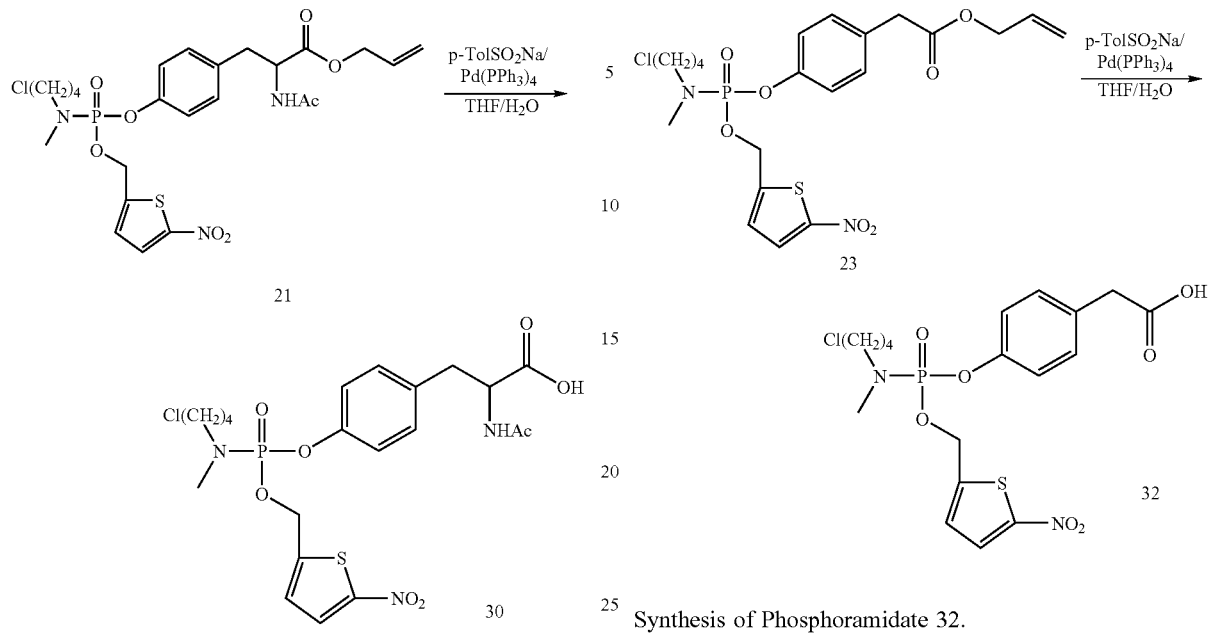

Synthesis of Phosphoramidate 30.
Phosphoramidate 30 was synthesized in a similar manner as described for 25.
$^1$H NMR (CDCl$_3$, TMS) d: 7.87–7.73 (m, 1H), 7.14–7.04 (m, 4H), 7.03–6.95 (m, 1H), 5.34–5.18 (m, 2H), 5.11–4.96 (m, 1H), 4.95–4.81 (m, 1H), 3.60–3.46 (m, 2H), 3.26–3.03 (4H), 2.85–2.67 (m, 3H), 2.05–1.92 (m, 3H), 1.84–1.62 (m, 4H) ppm. $^{31}$P NMR (TPPO) d: −19.41, −19.61 ppm. HPLC (gradient 30–100%, CH$_3$CN/H$_2$O-0.1% TFA, over 35 min): 13.10 min. MS (ESI) m/z: 548/550 (M+H).

Synthesis of Phosphoramidate 31.
Phosphoramidate 31 was synthesized in a similar manner as described for 25.
$^1$H NMR (CDCl$_3$, TMS) d: 7.26–7.04 (m, 5H), 6.60 (d, 1H, j=3.58 Hz), 5.43–5.19 (m, 2H), 5.06 (d, 2H, j=9.16 Hz), 3.62 (s, 2H), 3.51 (t, 2H), 3.18–2.96 (m, 2H), 2.71 (d, 3H, j=10.26 Hz), 1.77–1.55 (m, 4H) ppm. $^{31}$P NMR (TPPO) d: −19.01 ppm.

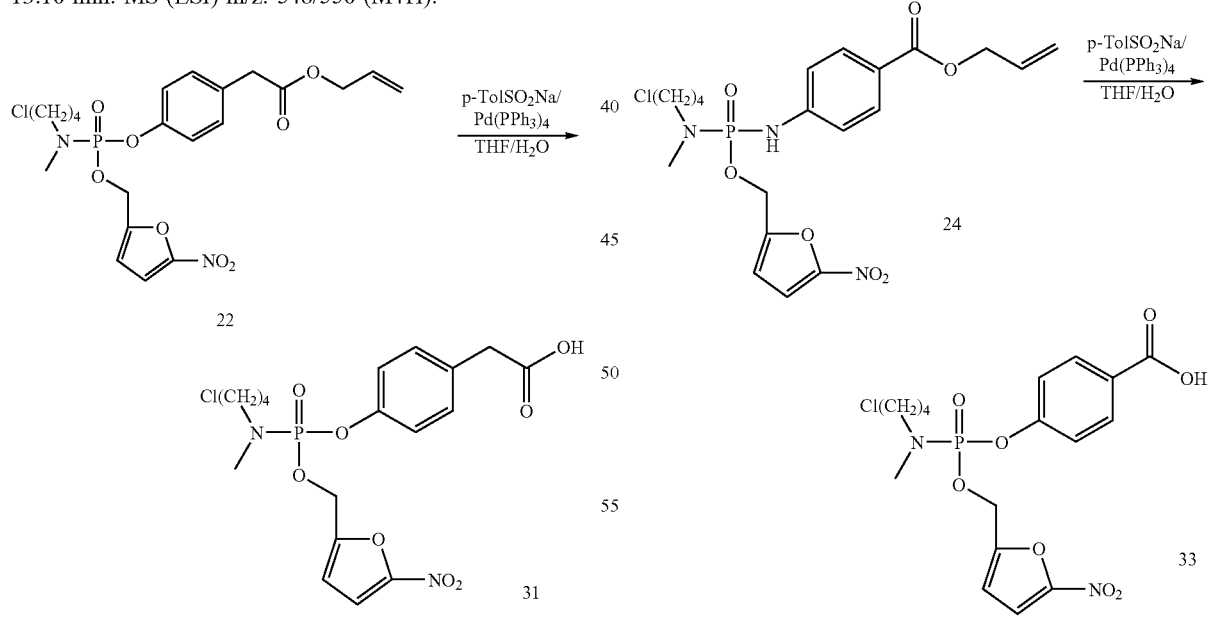

Synthesis of Phosphoramidate 32.
Phosphoramidate 32 was synthesized in a similar manner as described for 25.
$^1$H NMR (CDCl$_3$, TMS) d: 7.80 (d, 1H, j=4.12 Hz), 7.33–7.09 (m, 4H), 6.99 (d, 1H, j=4.12 Hz), 5.22 (d, 2H, j=8.52 Hz), 3.63 (s, 2H), 3.48 (t, 2H), 3.30–2.96 (m, 2H), 2.73 (d, 3H, j=10.25 Hz), 1.92–1.40 (m, 4H) ppm. $^{31}$P NMR (TPPO) d: −19.29 ppm. HPLC (gradient 30–100%, CH$_3$CN/H$_2$O-0.1% TFA, over 35 min): 15.13 min.

Synthesis of Phosphoramidate 33.
Phosphoramidate 33 was synthesized in a similar manner as described for 25.
$^1$H NMR (CDCl$_3$, TMS) d: 7.96 (d, 2H, j=8.6 Hz), 7.26 (d, 1H, j=3.67 Hz), 6.99 (d, 2H, j=8.6 Hz), 6.65 (d, 1H, j=3.67 Hz), 6.45–6.25 (m, 1H), 5.09 (d, 2H, j=9.43 Hz), 3.52

(t, 2H), 3.22–2.99 (m, 2H), 2.69 (d, 3H, j=10.53 Hz), 1.85–1.61 (m, 4H) ppm. $^{31}$P NMR (TPPO) d: –15.40 ppm HPLC (gradient 30–100% CH$_3$CN/H$_2$O-0.1% TFA, over 35 min): 9.13, 9.37 min. MS (ESI) m/z: 444/446 (M–H).

Synthesis of Phosphoramidate 36.

Diisopropylethyl amine (0.11 mL, 0.61 mmol) was added neat to a pre-cooled solution of phosphoramidate 26 (0.14 g,

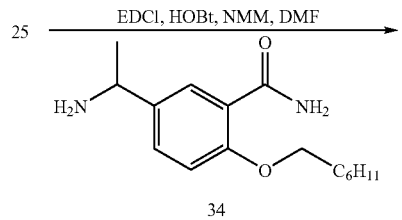

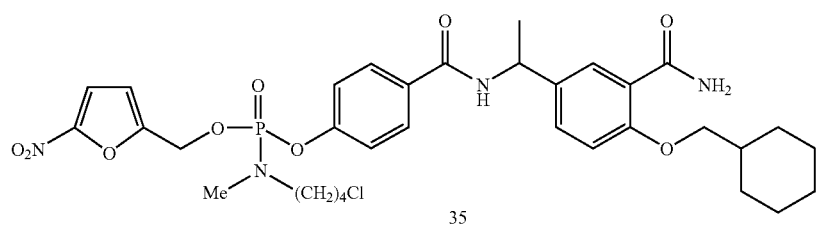

Synthesis of prodrug 35.

Phosphoramidate 25 (0.105 g, 0.23 mmol) was dissolved in 2 mL of dry DMF and cannulated to a mixture of benzylamine 34 (0.0735 g, 0.23 mmol), 4-methyl morpholine (0.06 mL, 0.588 mmol) and HOBT (0.0382 g, 0.28 mmol) in 3 ml of dry DMF at 0° C., followed by the addition of EDCI (0.0541 g, 0.28 mmol). Reaction was warmed up to room temperature and stirred overnight. Water was added to the reaction mixture and extracted with ethyl acetate. Organic extracts were combined, washed with saturated sodium bicarbonate, water, brine, dried over MgSO$_4$ and evaporated to dryness to yield a dark orange oil. Product was chromatographed on reverse phase silica using a 75:25 mixture of MeOH:H$_2$O, respectively to yield 35 (58.7 mg, 35% yield) as a white foam.

$^1$H NMR (CDCl$_3$, TMS) d: 8.25 (d, 1H), 7.72 (d, 2H, j=8.42 Hz), 7.50 (d, 1H), 7.24 (m, 3H), 6.95 (d, 2H, j=8.42 Hz), 6.63 (d, 1H, j=3.66 Hz), 5.28 (t, 1H), 5.07 (d, 2H, j=9.16 Hz), 3.93 (d, 2H), 3.52 (t, 2H), 3.09 (m, 2H), 2.70 (d, 3H), 1.87–1.58 (m, 14H), 1.48–0.85 (m, 4H). $^{31}$P NMR (TPPO) d: –21.2 ppm. HPLC (60:40 CH$_3$CN/H$_2$O-0.1% solution of TFA): 8.817 min. MS (ESI) m/z: 727/729 (M+Na), 705/707 (M+H). MS high resolution (ESI) m/z: calculated: 705.2456; obtained: 705.2432.

0.28 mmol), benzylamine 34 (0.08 g, 0.31 mmol) and PyBOP (0.14 g, 0.28 mmol) in 2 mL of dry DCM at 0° C. Reaction was stirred for 10 min at 0° C. and 30 minutes at room temperature. Reaction was quenched with saturated ammonium chloride and DCM. Layers were separated; organic layer was washed with brine, dried over MgSO$_4$ and evaporated to dryness to yield light yellow oil. Crude product was chromatographed using a mixture of 9:1 EtOAc/MeOH to yield 36 (0.16 g, 75% yield) as white foam.

$^1$H NMR (CDCl$_3$, TMS) d: 8.34–8.20 (m, 2H), 8.11–8.04 (m, 1H), 7.92–7.78 (bs, 1H), 7.71 (d, 2H, j=8.60 Hz), 7.63–7.43 (m, 3H), 7.28–7.24 (m, 2H), 6.95 (d, 1H, j=8.6 Hz), 6.8 (s, 1H), 6.27 (d, 1H, j=7.79 Hz), 5.84–5.67 (bs, 1H), 5.43–5.16 (m, 3H), 3.94 (s, 3H), 3.92 (s, 3H), 3.47 (t, 2H), 3.21–2.94 (m, 2H), 2.69 (d, 3H, j=10.52 Hz), 1.96–1.49 (m, 14H), 1.41–0.93 (m, 5H). $^{31}$P NMR (TPPO) d: –18.82 ppm. HPLC (gradient 30–100%, CH$_3$CN/H$_2$O-0.1% TFA, over 35 min): 24.05 min. MS (ESI) m/z: 802/804 (M+Na), 780/782 (M+H). MS High Resolution (ESI) m/z: calculated: 780.3181; obtained: 780.3168.

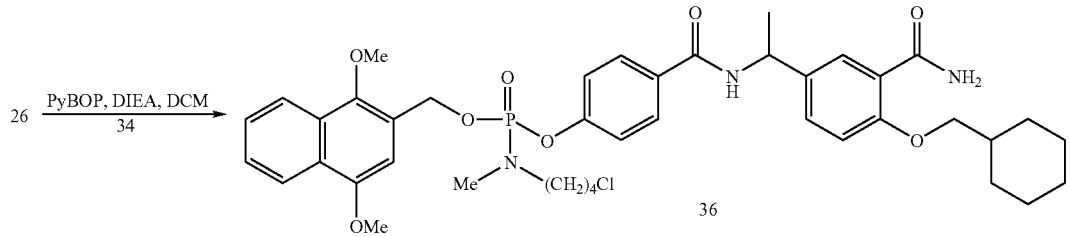

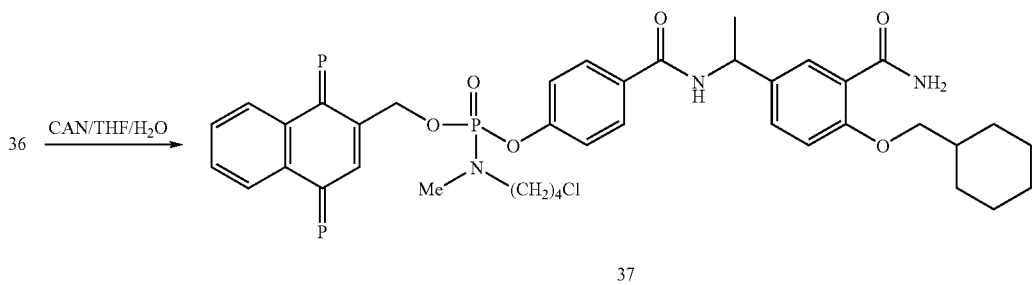

Synthesis of Prodrug 37.

Ceric ammonium nitrate (0.11 g, 0.21 mmol) was dissolved in 1 mL of H₂O and added slowly to a solution of phosphoramidate 36 (0.08 g, 99.83 mmol) in 3.7 mL of acetonitrile and 1.9 mL of H₂O. Reaction was stirred for 1.5 hours and then quenched by the addition of saturated ammonium chloride and extracting it with EtOAc. Organic layers were combined washed with brine, dried over MgSO₄ and evaporated to dryness to yield light yellow oil. Crude product was chromatographed using a mixture of 9:1 EtOAc/MeOH to yield 37 (0.03 g, 65% yield) as light yellow foam.

$^1$H NMR (CDCl₃, TMS) d: 8.34–8.21 (m, 2H), 8.11–8.04 (m, 1H), 7.92–7.78 (bs, 1H), 7.72 (d, 2H, j=8.60 Hz), 7.28–7.24 (m, 2H), 6.95 (d, 2H, j=8.60 Hz), 6.94 (d, 1H, j=8.6 Hz), 6.9 (s, 1H), 6.41 (d, 1H, j=8.6 Hz), 5.84–5.67 (bs, 1H), 5.43–5.16 (m, 3H), 3.93 (s, 3H), 3.91 (s, 5H), 3.47 (t, 2H), 3.21–2.94 (m, 2H), 2.69 (d, 3H, j=10.52 Hz), 1.96–1.49 (m, 14H), 1.41–0.93 (m, 5H). $^{31}$P NMR (TPPO) d: −19.0 HPLC (gradient 30–100%, CH₃CN/H₂O-0.1% TFA, over 35 min): 21.45 min. MS (ESI) m/z: 772/774 (M+Na), 750/752 (M+H). MS high resolution (ESI) m/z: calculated: 750.2711; obtained: 750.2708.

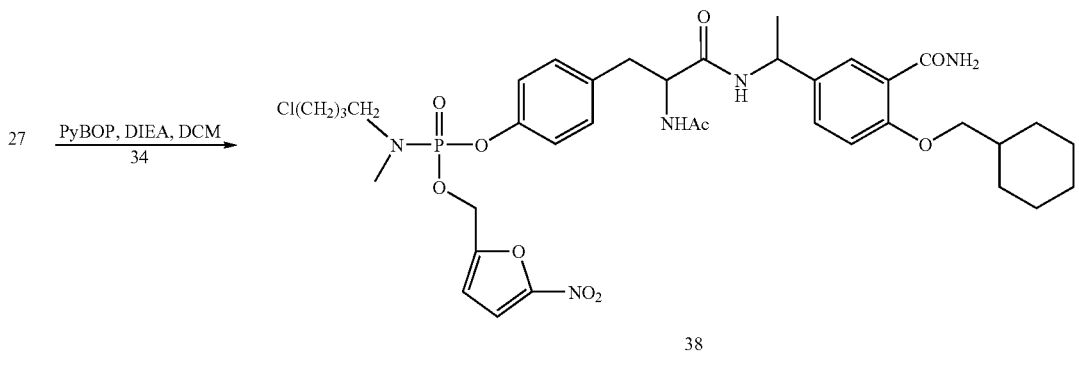

Synthesis of Prodrug 38.

Prodrug 38 was synthesized in a similar manner as described for 36.

$^1$H NMR (CDCl₃, TMS) d: 8.26–8.11 (m, 1H), 8.09–7.99 (m, 1H), 7.95–7.76 (m, 1H), 7.24–7.09 (m, 2H), 7.08–6.99 (m, 2H), 6.96–6.82 (m, 1H), 6.72–6.55 (m, 1H), 6.50–6.20 (m, 1H), 6.18–6.54 (m, 1H), 5.16–4.82 (m, 3H), 4.79–4.46 (m, 1H), 4.03–3.78 (m, 2H), 3.62–3.43 (m, 2H), 3.15–2.81 (m, 5H), 2.80–2.51 (m, 3H), 2.04–1.89 (m, 3H), 1.87–1.56 (m, 10H), 1.49–0.90 (m, 8H) ppm. $^{31}$P NMR (TPPO) d: −18.94 ppm. HPLC (gradient 30–100%, CH₃CN/H₂O-0.1% TFA, over 35 min): 19.03, 19.25 min. MS (ESI) m/z: 790/792 (M+H), 812/814 (M+Na) MS High Resolution (ESI) m/z: calculated: 790.2984; obtained: 790.2981.

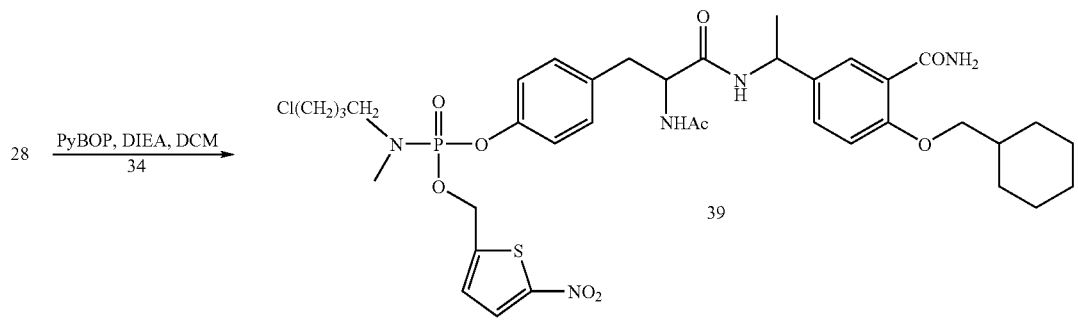

Synthesis of Prodrug 39.

Prodrug 39 was synthesized in a similar manner as described for 35.

$^1$H NMR (CDCl$_3$, TMS) d: 8.21–8.09 (m, 1H), 8.08–7.98 (m, 1H), 7.93–7.71 (m, 2H), 7.23–7.04 (m, 6H), 6.66–6.47 (m, 1H), 6.36–6.16 (m, 1H), 6.11–5.80 (m, 1H), 5.30–5.15 (m, 2H), 5.14–4.81 (m, 1H), 4.75–4.48 (m, 1H), 4.02–3.85 (m, 2H), 3.62–3.42 (m, 2H), 3.13–2.82 (m, 5H), 2.82–2.58 (m, 3H), 2.04–1.92 (m, 3H), 1.84–1.53 (m, 9H), 1.51–0.87 (m, 9H) ppm. $^{31}$P NMR (TPPO) d: −19.16 ppm. HPLC (gradient 30–100%, CH$_3$CN/H$_2$O-0.1% TFA, over 35 min): 20.17, 20.35 min. MS (ESI) m/z: 806/808 (M+H), 828/830 (M+Na) MS High Resolution (ESI) m/z: calculated: 806.2755; obtained: 806.2758.

Synthesis of Prodrug 40.

Prodrug 40 was synthesized in a similar manner as described for 35.

$^1$H NMR (CDCl$_3$, TMS) d: 8.10–8.00 (m, 1H), 7.99–7.86 (m, 1H), 7.45–7.09 (m, 7H), 6.98–6.85 (m, 1H), 6.69–6.56 (m, 1H), 6.05–5.89 (m, 1H), 5.87–5.69 (m, 1H), 5.19–4.95 (m, 3H), 4.02–3.81 (m, 2H), 3.64–3.29 (m, 4H), 3.26–2.92 (m, 2H), 2.87–2.52 (m, 3H), 2.02–1.57 (m, 11H), 1.54–0.89 (m, 6H). $^{31}$P NMR (TPPO) d: −18.91, −18.99 ppm. HPLC (gradient 30–100%, CH$_3$CN/H$_2$O-0.1% TFA, over 35 min): 20.65 min. MS (ESI) m/z: 719/721 (M+H), 741/743 (M+Na) MS High Resolution (ESI) m/z: calculated: 719.2613; obtained: 719.2600.

Synthesis of Prodrug 41.

Prodrug 41 was synthesized in a similar manner as described for 35.

$^1$H NMR (CDCl$_3$, TMS) d: 8.14–8.00 (m, 1H), 7.93–7.80 (m, 1H), 7.81–7.69 (m, 1H), 7.42–7.30 (m, 1H), 7.27–7.06 (m, 5H), 7.04–6.93 (m, 1H), 6.93–6.81 (m, 1H), 6.23–5.99 (m, 2H), 5.27–5.15 (m, 2H), 5.13–4.93 (m, 1H), 3.99–3.81 (m, 2H), 3.60–3.38 (m, 4H), 3.21–2.98 (m, 2H), 2.85–2.62 (m, 3H), 1.92–1.59 (m, 11H), 1.50–0.97 (6H). $^{31}$P NMR (CDCl$_3$, TPPO) d: −19.26 HPLC (gradient 30–100%, CH$_3$CN/H$_2$O-0.1% TFA, over 35 min): 21.77 min. MS (ESI) m/z: 735/737 (M+H), 757/759 (M+Na). MS High Resolution (ESI) m/z: calculated: 735.2384; obtained: 735.2358.

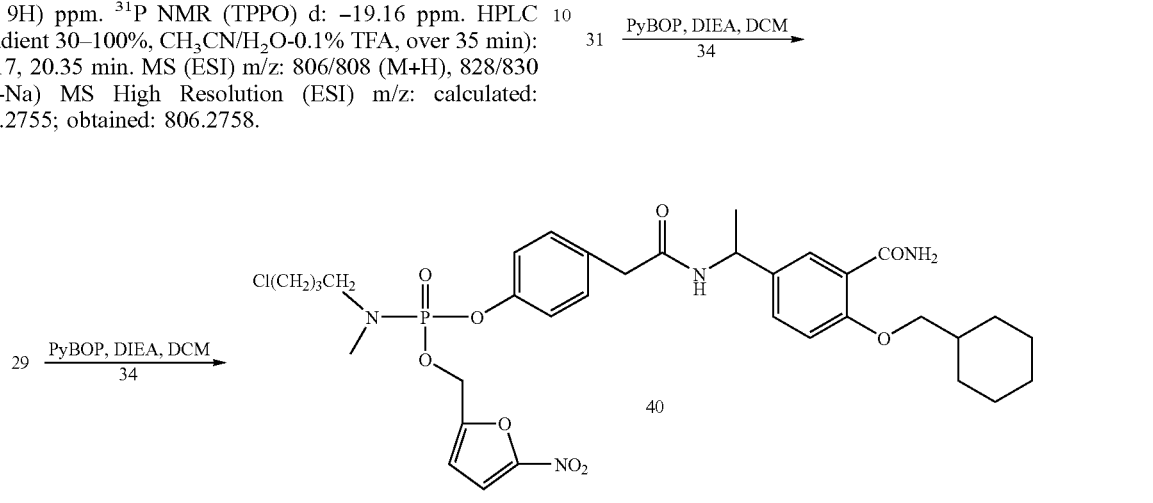

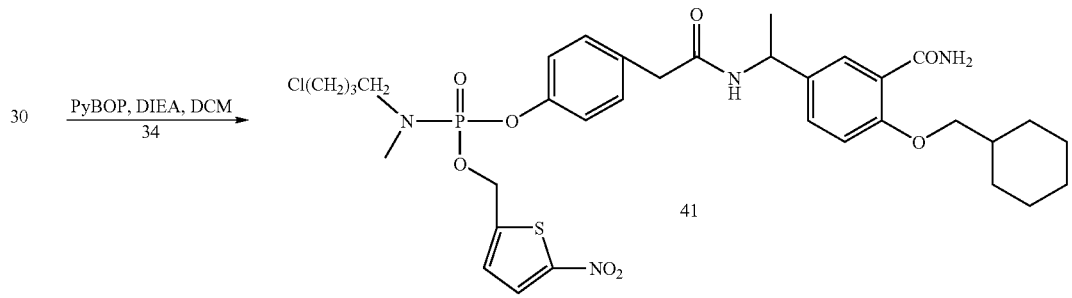

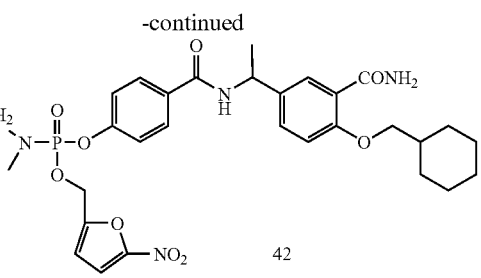

Synthesis of Prodrug 42.

Prodrug 42 was synthesized in a similar manner as described for 35.

$^1$H NMR (CDCl$_3$, TMS) d: 8.22 (d, 1H, j=2.01 Hz), 7.96–7.81 9m, 1H), 7.61 (d, 2H, j=8.15 Hz), 7.56–7.40 (m, 1H), 7.25–7.13 (m, 1H), 6.92 (d, 2H, j=8.15 Hz), 6.82–6.66 (m, 1H), 6.66–6.53 (m, 1H), 6.27–6.00 (m, 2H), 5.35–5.10

(m, 1H), 5.03 (d, 2H, j=9.25 Hz), 3.90 (d, 2H, j=5.86 Hz), 3.48 (t, 2H), 3.18–2.92 (m, 2H), 2.64 (d, 3H, j=10.53 Hz), 1.94–1.47 (m, 10H), 1.38–0.98 (n, 7H) ppm. $^{31}$P NMR (CDCl$_3$, TPPO) d: −14.96 ppm. HPLC (gradient 30–100%, CH$_3$CN/H$_2$O-0.1% TFA, over 35 min): 17.28 min. MS (ESI) m/z: 704/706 (M+H), 726/728 (M+Na). MS High Resolution (ESI) m/z: calculated: 704.2616; obtained: 704.2633.

Growth Inhibition in L1210 Mouse Leukemia Cells

Stock solutions of drugs were prepared in absolute ethanol, and serial dilutions of drug were prepared in ethanol. L1210 cells were suspended in Fisher's medium supplemented with 10% horse serum, 1% glutamine, and 1% antibiotic-antimycotic solution to give 10 mL volumes of cell suspension at a final density of 3–6×10$^4$ cells/mL. Appropriate volumes of the drug solution were transferred to the cell suspensions, and incubation was continued for 2, 8, 24, or 48 hours. The cells were spun down, resuspended in fresh drug-free medium and returned to the incubator. Final cell counts were determined 48 hours after the start of drug treatment. The data were analyzed by sigmoidal curve fit of cell count vs. Log (drug concentration) and the results expressed as the IC$_{50}$ (the drug concentration that inhibits cell growth to 50% of control value).

| Compound | IC$_{50}$ nM | | | |
|---|---|---|---|---|
|  | 2 h | 8 h | 24 h | 48 h |
| 3 | 116 | 47 | 7.2 | 2.3 |
| 5 | 44 | 16 | 3.1 | .63 |
| 6 | 34 | 48 | 4.8 | 1.6 |
| 5-FU | 2500 | 1010 | 360 | 200 |
| FUdR | 45 | 23 | 4.1 | .64 |

Luciferase Inhibition on Transfected J77 Cells.

J77 cells (2×10$^7$ cells in 500 mL of FBS-free RPMI media) were transfected with 15 mg of NF-AT-Luciferase plasmid. Cells were transferred to a flask with 10 mL of complete RPMI media and incubated for 24 hours. After this time cells were spun down, resuspended in 12 mL of complete RPMI media and divided into a 6-well plate (2 mL/well). Drug stock solutions in DMSO were made and each well was treated with a different concentration and incubated for 2 hours. Each well was then treated with 10 mL of a mixture of 1.25 mg of PMA and 9 mg of Ionomycin in 115 mL of FBS-free RPMI, followed by the addition of 2 mg of Anti-CD3. Cells were incubated for 6 hours, spun down, washed with PBS, lysed for 15 min and centrifuged. Supernatant was collected and stored at −78° C. overnight. Luciferase activity was measured using a luminometer with a mixture of 50 mL of luciferase substrate and 10 ml of supernatant.

| Compound | IC$_{50}$ (uM) |
|---|---|
| 35 | 34.1 |
| 37 | 4.2 |
| 38 | 5.6 |
| 40 | 3.4 |
| 42 | 15.0 |

Tritium Assay in L1210, LM and LM (TK−) Cells

Stock solutions of drugs were prepared in absolute ethanol. L1210 cells were suspended in fisher's medium, LM and LM (TK−) cells were suspended in minimum essential medium to give a final density of 11.24×10$^6$ cells/mL. Aliquots (445 mL) of the cell suspension were placed in ependorf tubes, followed by addition of 5 mL of drug solution and incubated at 37° C. for 2 hours. Tritium release reaction was started by the addition of 50 mL of serum free media containing 1 mCi [5-$^3$H]dCyt in a 0.5 mM dCyt solution. Allowed reaction to incubate for 60 min in a shaking water bath at 37° C. Reaction was terminated by transferring 100 mL of the reaction mixture to ependorf tubes containing 100 mL of a 20% mixture of activated charcoal suspension in 4% aqueous perchloric acid. Tubes were vigorously vortexed, then centrifuged in a microfuge. Radioactivity of 100 mL of the supernatant was measured using a scintillation spectrometer. The data were analyzed by sigmoidal curve fit of CMP vs. Log (drug concentration) and the results expressed as the IC$_{50}$ (the drug concentration that inhibits cell growth to 50% of control value).

| Compound | IC$_{50}$ nM | | |
|---|---|---|---|
|  | L1210 | LM | LM(TK−) |
| 3 | 46 | 711 | 1280 |
| FudR | 8 | 59 | 3670 |

Pharmaceutical Formulations

The following parenteral formulations are prepared for use in cancer therapy.

| Compound | Mass/Dose (mg) | Carrier(s) |
|---|---|---|
| 3 | 25 | isotonic saline |
| 5 | 50 | isotonic saline + DMSO |
| 6 | 100 | 5% glucose |
| 35 | 550 | 5% glucose + cyclodextrin |
| 37 | 180 |  |
| 38 | 300 | lipid emulsion |
| 40 | 40 | isotonic saline |
| 42 | 450 | isotonic saline + cyclodextrin |

What is claimed is:

1. A compound of the formula

wherein
R is C$_1$–C$_4$ alkyl or —(CH$_2$)$_n$X;
n is 4 or 5;

X is an electrophilic group capable of being nucleophilically displaced from its bonded carbon atom;
halo is chloro, bromo, or iodo; and
$R_rCH_2$— is a biologically labile ester forming group.

2. The compound of claim 1 wherein n is 4.

3. The compound of claim 1 wherein n is 5.

4. The compound of claim 1 wherein R is methyl.

5. The compound of claim 1 wherein halo is chloro.

6. The compound of claim 1 wherein X is chloro or bromo.

7. A method for preparing a phosphoramidate prodrug for enhanced intracellular delivery of a drug as a phosphate ester or amide, said method comprising the steps of reacting a hydroxy functional or amino functional drug compound of the formula Drug-ZH with a compound of the formula $R_rCH_2OP(halo)NR(CH_2)_nX$ to form an intermediate compound of the formula $R_rCH_2OP(Z\text{-Drug})NR(CH_2)_nX$ and oxidizing the intermediate compound to form the phosphoramidate prodrug of the formula $R_rCH_2OP(O)(Z\text{-Drug})NR(CH_2)_nX$ wherein in each of said formulas
R is $C_1$–$C_4$ alkyl or —$(CH_2)_nX$;
n is 4 or 5;
Z is oxygen or nitrogen;
X is an electrophilic group capable of being nucleophilically displaced from its bonded carbon atom;
halo is chloro, bromo, or iodo; and
$R_rCH_2$— is a biologically labile ester forming group.

8. The method of claim 7 wherein Drug-ZH is an amino acid, or a biologically active peptide or peptidomimetic.

9. The method of claim 8 wherein Drug-ZH is a peptidomimetic of the formula

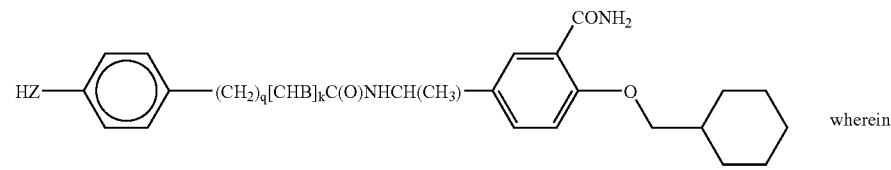

wherein
Z is oxygen or nitrogen;
q and k are independently 1 or 0; and
B is hydrogen, amino, protected amino, or $C_1$–$C_4$ alkanoylamino.

10. The method of claim 7 wherein Drug-ZH is a biologically active nucleotide analog.

11. A method for preparing a compound of the formula $R_rCH_2OP(O)_m(halo)NR(CH_2)_nX$ comprising the steps of reacting a compound of the formula $P(O)_m(halo)_3$ with 1) an alcohol of the formula $R_rCH_2OH$ and 2) an amine of the formula $HNR(CH_2)_nX$, each in the presence of an acid scavenger, wherein in each of said formulas
m is 0 or 1;
R is $C_1$–$C_4$ alkyl or —$(CH_2)_nX$;
n is 4 or 5;
X is an electrophilic group capable of being nucleophilically displaced from its bonded carbon atom;
halo is chloro, bromo, or iodo; and
$R_rCH_2$— is a biologically labile ester forming group.

12. A method for preparing a phosphoramidate prodrug of the formula $R_rCH_2OP(O)(Z\text{-Drug})NR(CH_2)_nX$ for enhanced intracellular delivery of a compound of the general formula Drug-Z$(PO_3)^{2-}$ said method comprising the steps of reacting a hydroxy functional or amino functional drug compound of the formula Drug-ZH with a compound of the formula $R_rCH_2OP(O)(halo)NR(CH_2)_nX$ to form the prodrug; wherein in each of said formulas
R is $C_1$-C alkyl or —$(CH_2)_nX$;
n is 4 or 5;
Z is oxygen or nitrogen;
X is an electrophilic group capable of being nucleophilically displaced from its bonded carbon atom;
halo is chloro, bromo, or iodo; and
$R_rCH_2$— is a biologically labile ester forming group.

13. The compound of claim 1 wherein $R_r$ is nitroaryl, indanyl, naphthoquinolyl, or perhydrooxazine; halo is chloro; R is alkyl; n is 4; and X is halo.

14. The compound of claim 13 wherein $R_r$ is 5-nitrofur-2-yl; R is methyl; and X is chloro.

15. The method of claim 7 wherein $R_r$ is nitroaryl, indanyl, naphthoquinolyl, or perhydrooxazine; halo is chloro; R is alkyl; n is 4; and X is halo.

16. The method of claim 11 wherein $R_r$ is nitroaryl, indanyl, naphthoquinolyl, or perhydrooxazine; halo is chloro; R is alkyl; n is 4; and X is halo.

17. The method of claim 12 wherein $R_r$ is nitroaryl, indanyl, naphthoquinolyl, or perhydrooxazine; halo is chloro; R is alkyl; n is 4; and X is halo.

* * * * *

UNITED STATES PATENT AND TRADEMARK OFFICE
CERTIFICATE OF CORRECTION

PATENT NO. : 7,173,020 B2  
APPLICATION NO. : 11/053024  
DATED : February 6, 2007  
INVENTOR(S) : Borch et al.

Page 1 of 1

It is certified that error appears in the above-identified patent and that said Letters Patent is hereby corrected as shown below:

Column 61, line 43 please replace formula with formula below

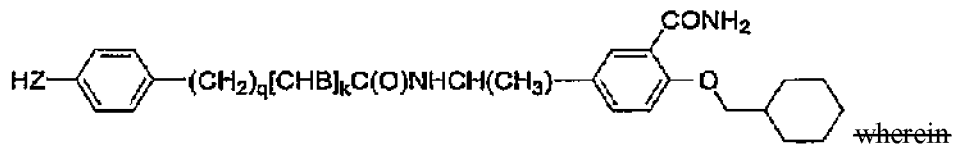

Signed and Sealed this

First Day of May, 2007

JON W. DUDAS  
*Director of the United States Patent and Trademark Office*